US006551793B1

(12) United States Patent
Vainstein et al.

(10) Patent No.: US 6,551,793 B1
(45) Date of Patent: Apr. 22, 2003

(54) CAROTENOID-ASSOCIATED PROTEINS USEFUL FOR HIGH CAROTENOID ACCUMULATION AND PRODUCTION IN PLANTS AND OTHER ORGANISMS

(75) Inventors: Alexander Vainstein, Rehovot (IL); Michael Vishnevetsky, Kiryat Arba (IL); Marianna Ovadis, Rehovot (IL); Hanan Itzhaki, Nes Ziona (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/326,806

(22) Filed: Jun. 4, 1999

Related U.S. Application Data

(63) Continuation of application No. PCT/IL97/00399, filed on Dec. 4, 1997.
(60) Provisional application No. 60/032,421, filed on Dec. 5, 1996, now abandoned.

(51) Int. Cl.[7] .................................. C12P 23/00
(52) U.S. Cl. .................. 435/67; 435/468; 435/471; 435/419; 435/320.1; 536/23.1; 536/23.2; 536/23.6; 536/24.1
(58) Field of Search ................ 536/23.1, 23.2, 536/23.6, 24.1; 435/320.1, 67, 252.3, 254.11, 419, 468, 471

(56) References Cited

U.S. PATENT DOCUMENTS 5,429,939 A  7/1995 Misawa et al.

OTHER PUBLICATIONS

Vishnevetsky, M. GenBank Accession No. X95593 (1996), Sep. 1996.*

Deruere et al. Structure and Expression of Two Plant Genes Encoding Chromoplast–Specific Proteins. Biochem. Biophys. Res. Comm. (1994) 199(3): 1144–1150, Mar. 1994.*

Schantz, R. GenBank Accession No. X97118 (1996), Apr. 1996.*

Kim et al. Structure of the Mouse IL–10 Gene and Chromosomal Localization of the Mouse and Human Genes. J. of Immunology (1992) 148(11): 3618–3623, Jun. 1992.*

Harris et al. Cloning and Characterization of the Zona Pellucida genes and cDNAs from a variety of mammalian species. DNA Sequence (1994) 4: 361–393.*

Matsudaira, P. Limited N–terminal sequence analysis. Methods Enzymol (1990) 182:602–13.*

Wozney JM. Using purified protein to clone its gene. Methods Enzymol (1990) 182:738–51.*

Maniatis et al. Molecular Cloning: A Laboratory Manual (1982) Cold Spring Harbor Laboratory Press. pp 404–433, 1982.*

Vishnevetsky et al. Molecular Cloning of a carotenoid–associated protein from Cucumis sativus corollas: homolgous genes involved in carotenoid sequestration in chromoplasts. The Plant Journal (1996) 10(6): 1111–1118, Dec. 1996.*

(List continued on next page.)

*Primary Examiner*—Ponnathapu Achutamurthy
*Assistant Examiner*—Kathleen Ken
(74) *Attorney, Agent, or Firm*—John P. White; Cooper & Dunham LLP

(57) ABSTRACT

A method for production of high amounts of carotenoids in plants, bacteria or cells. Carotenoid-associated proteins CHRC and CHRD isolated from corollas of *Cucumis sativus*, chrc gene, CHRC deduced sequence, the molecular cloning, cDNA and RNA. A new CHRC promoter able to direct expression for foreign genes. The cloned promoter comprising approximately 3.5 Kb of the CHRC upstream region.

15 Claims, 11 Drawing Sheets

OTHER PUBLICATIONS

Adam, Z., et al. (1993). Biogenesis of a photosystem I light–harvesting complex. *Plant Physiol.* 102: 35–43 (Exhibit 1).

Badillo, A., et al. (1995). Structure of a functional geranylgeranyl pyrophosphate synthase gene from *Capsicum annuum*. *Plant Mol. Biol.* 27: 425–428 (Exhibit 2).

Bartley, G.E., et al. (1995). Plant carotenoids: pigments for photoprotection, visual attraction, and human health. *Plant Cell* 7: 1027–1038 (Exhibit 3).

Bouvier, F., et al. (1994). Xanthophyll biosynthesis in chromoplasts: isolation and molecular cloning of an enzyme catalyzing the conversion of 5,6–epoxycarotenoid into ketocarotenoid. *Plant J.* 6: 45–54 (Exhibit 4).

Cleveland, D.W., et al. (1977). Peptide mapping by limited proteolysis in sodium dodecyl sulfate and analysis by gel electrophoresis. *J. Biol. Chem.* 252: 1102–1106 (Exhibit 5).

Deruere, J., et al. (1994). Fibril assembly and carotenoid overaccumulation in chromoplasts: a model for supramolecular lipoprotein structure. *Plant Cell* 6: 119–133 (Exhibit 6).

D'Souza, S.E., et al. (1991). Arginyl–glycyl–aspartic acid (RGD): a cell adhesion motif. *Trends in Biol. Sci.* 16: 246–250 (Exhibit 7).

Emter, O., et al. (1990) Specific carotenoids and proteins as prerequisites for chromoplast tubule formation. *Protoplasma* 157: 128–135 (Exhibit 8).

Giuliano, G. et al. (1993) Regulation of carotenoid biosynthesis during tomato development. *Plant Cell* 5: 379–387 (Exhibit 9).

Hansmann, P., et al. (1982). Composition and molecular structure of chromoplast globules of *Viola tricolor*. Plant Cell Rep. 1: 111–114 (Exhibit 10).

Hofmann, K., and W. Stoffel. (1993). A database of membrane spanning protein segments. *TMpred Biol. Chem. Hoppe. Seyler.* 374: 166 (Abstract) (Exhibit 11).

Houlne, G., et al. (1994). A chromoplast–specific protein in *Capsicum annuum*: characterization and expression of the corresponding gene. *Curr. Genet.* 26: 524–527 (Exhibit 12).

Huang, L., et al. (1992). Deletion mutants of chlorophyll a/b binding proteins are efficiently imported into chloroplasts but do not integrate into thylakoid membranes. *Plant Physiol.* 99: 247–255 (Exhibit 13).

Karvouni, Z., et al. 1995. Isolation and characterisation of a melon cNA clone encoding phytoene synthase. *Plant Mol. Biol.* 27: 1153–1162 (Exhibit 14).

Kyte, J. and R.F. Doolittle. (1982). A simple method for displaying the hydropathic character of a protein. *J. Mol. Biol.* 157: 105–132 (Exhibit 15).

Levy, M. and Z. Adam. (1995). Mutations in the processing site of the precursor of ribulose–1, 5–bisphosphate carboxylase/oxygenase small subunit: effects on import, processing, assembly and stability. *Plant Mol. Biol.* 29: 53–61 (Exhibit 16).

Marano, M.R., et al. (1993). The path of chromoplast development in fruits and flowers. *Plant Sci.* 94: 1–17 (Exhibit 17).

Matsudaira, P. (1987). Sequence from picomole quantities of proteins electroblotted onto polyvinylidene difluoride membranes. *J. Biol. Chem.* 262: 10035–10038 (Exhibit 18).

Newman, L.A., et al. (1989). Synthesis of two chromoplast–specific proteins during fruit development in *Capsicum annuum*. *Plant Physiol.* 91: 455–458 (Exhibit 19).

Oren–Shamir, M., et al. (1993). Occurrence of the chromoplast protein ChrA correlates with a fruit–color gene in *Capsicum annuum*. *Plant Mol. Biol.* 21:549–554 (Exhibit 20).

Rost, B. and C. Sander. (1993). Prediction of protein secondary structure at better than 70% accuracy. *J. Mol. Biol.* 232:584–599 (Exhibit 21).

Smirra, I., et al. (1993). Isolation and characterization of a chromoplast–specific carotenoid–associated protein from *Cucumis sativus* corollas. *Plant Physiol.* 102:491–496 (Exhibit 22).

Vainstein, A., et al. (1994). Cromoplast biogenesis in *Cucumis sativus* corollas. *Plant Sci.* 104: 321–326 (Exhibit 23).

Van Tunen, A.J., et al. (1988). Cloning of the two chalcone flavanone isomerase genes from *Petunia hybrida* : coordinate, light–regulated and differential expression of flavonoid genes. *EMBO* 7: 1257–1263 (Exhibit 24).

* cited by examiner

CHRD

SEQUENCE LISTING

<160> NUMBER OF SEQ ID NOS: 10

<210> SEQ ID NO 1
<211> LENGTH: 1309
<212> TYPE: DNA
<213> ORGANISM: Cucumis sativus

<400> SEQUENCE: 1

```
agtaaatccc agtccttcag tttgtgcttt tgtgtgtttt gtttctctga tttacggaat      60
ttggaaataa ttctatggcg tttgtttcta aattcaatca acttccgtgc aagactctcg     120
cactcaatcc accacaacct caattgactt ctaagccttc ggttttcccc atcgcttcga     180
ttggggctac cgccagagcc gcggcgggga agtcactgat ctcagttagg cctgcgttca     240
aggtccgtgc ggtgttaaac gatgacgagt gggggagga taaggatgag aagtatggag      300
atgattcgtc tgtggcggta gctgaaaagg aggaggaaaa gcctctggag ccatccgaga     360
tttataaact gaagaaggcg ttggtggact cgttttactt gaccgatcgt ggattacgag     420
tgtccagaga tactagggcg gagattgtcg agctgattac gcaactggaa tcgaagaacc     480 caaccctgc tcctactgag gccctgactc tgctcaacgg caagtggatt ctagcgtaca      540
```

```
caactttcgc gggtctgttc ccgttgttgt ctaggaatttt gccattggtc aaagtggagg    600
aaatttcaca gacaattgat tcagagaavv tcaccgtcca aaactctgtc cagttttccg    660
gtcctctagc caccacttcc attactacca atgcaaagtt tgaagttcga agtcccctgc    720
gtgtacatat caaattcgaa gaaggtgtca ttggaactcc ccagctgacg gattcgatag    780
tgataccaga taatgtggac tttcttgggc agaagattga ctttacacca ttcaatggta    840
tcatatcttc ccttcaagac actgcttcaa atgtagccaa gacgatttcg agtcaaccac    900
caatcaagtt ctcaatctca aacacgaggg tagagtcttg gttgctaact acttatcttg    960
atgaagatct tcgaatttca cgaggagatg gtggtagcgt gttcgtactc ctcaaggaag   1020
gcagttcttt cttgtctctc taaacaccct tactcttctc actataaagg gttcatagga   1080
aactgaatta ttattcaagg atgttttttaa acgtgttgta gtttcttatc aaatagtgaa   1140
tgatattgcc ttctgttcaa agggccagct tcaattagct tcatcttctt ttaaatcact   1200
agttacttga atttctgttg agaaaataaa cattgtttat atttaccca tactgtacca   1260
aaagccaaaa gttaaaccaa aacgtgtgaa aagcttggaa gggcttgac               1309
```

<210> SEQ ID NO 2
<211> LENGTH: 322
<212> TYPE: PRT
<213> ORGANISM: Cucumis sativus

<400> SEQUENCE: 2

```
Met Ala Phe Val Ser Gln Phe Asn Gln Leu Pro Cys Lys Thr Leu Ala
  1               5                  10                  15

Leu Asn Pro Pro Gln Pro Gln Leu Thr Ser Lys Pro Ser Val Phe Pro
             20                  25                  30

Ile Ala Ser Ile Gly Ala Thr Ala Arg Ala Ala Ala Gly Lys Ser Leu
         35                  40                  45

Ile Ser Val Arg Pro Ala Phe Lys Val Arg Ala Val Leu Asn Asp Asp
     50                  55                  60

Glu Trp Gly Glu Asp Lys Asp Glu Lys Tyr Gly Asp Asp Ser Ser Val
 65                  70                  75                  80

Ala Val Ala Glu Lys Glu Glu Lys Pro Leu Glu Pro Ser Glu Ile
                 85                  90                  95

Tyr Lys Leu Lys Lys Ala Leu Val Asp Ser Phe Tyr Gly Thr Asp Arg
            100                 105                 110

Gly Leu Arg Val Ser Arg Asp Thr Arg Ala Glu Ile Val Glu Leu Ile
        115                 120                 125

Thr Gln Leu Glu Ser Lys Asn Pro Thr Pro Ala Pro Thr Glu Ala Leu
    130                 135                 140

Thr Leu Leu Asn Gly Lys Trp Ile Leu Ala Tyr Thr Thr Phe Ala Gly
145                 150                 155                 160

Leu Phe Pro Leu Leu Ser Arg Asn Leu Pro Leu Val Lys Val Glu Glu
                165                 170                 175

Ile Ser Gln Thr Ile Asp Ser Gly Asn Leu Thr Val Gln Asn Ser Val
            180                 185                 190

Gln Phe Ser Gly Pro Leu Ala Thr Thr Ser Ile Thr Thr Asn Ala Lys
        195                 200                 205

Phe Glu Val Arg Ser Pro Leu Arg Val His Ile Lys Phe Glu Glu Gly
    210                 215                 220

Val Ile Gly Thr Pro Gln Leu Asp Ser Ile Val Leu Pro Asp Asn
225                 230                 235                 240
```

```
Val Asp Phe Leu Gly Gln Lys Ile Asp Phe Thr Pro Phe Asn Gly Ile
            245                 250                 255

Ile Ser Ser Leu Gln Asp Thr Ala Ser Asn Val Ala Lys Thr Ile Ser
            260                 265                 270

Ser Gln Pro Pro Ile Lys Phe Ser Ile Ser Asn Thr Arg Val Glu Ser
            275                 280                 285

Trp Leu Leu Thr Thr Tyr Leu Asp Glu Asp Leu Arg Ile Ser Arg Gly
            290                 295                 300

Asp Gly Gly Ser Val Phe Val Leu Leu Lys Glu Gly Ser Ser Phe Leu
305                 310                 315                 320

Ser Leu

<210> SEQ ID NO 3
<211> LENGTH: 322
<212> TYPE: PRT
<213> ORGANISM: Capsicum annuum

<400> SEQUENCE: 3

Met Ala Ser Ile Ser Ser Leu Asn Gln Ile Pro Cys Lys Thr Leu Gln
  1               5                  10                  15

Ile Thr Ser Gln Tyr Ser Lys Ile Ser Ser Leu Pro Leu Thr Ser Pro
             20                  25                  30

Asn Phe Pro Ser Lys Thr Glu Leu His Arg Ser Ile Ser Ile Lys Glu
         35                  40                  45

Phe Thr Asn Pro Lys Pro Lys Phe Thr Ala Gln Ala Thr Asn Tyr Asp
     50                  55                  60

Lys Glu Asp Glu Trp Gly Pro Glu Leu Glu Gln Ile Asn Pro Gly Gly
 65                  70                  75                  80

Val Ala Val Val Glu Glu Pro Pro Lys Glu Pro Ser Glu Met Glu
                 85                  90                  95

Lys Leu Lys Lys Gln Leu Thr Asp Ser Phe Tyr Gly Thr Asn Arg Gly
            100                 105                 110

Leu Ser Ala Ser Ser Glu Thr Arg Ala Glu Ile Val Glu Leu Ile Thr
            115                 120                 125

Gln Leu Glu Ser Lys Asn Pro Thr Pro Ala Pro Thr Glu Ala Leu Ser
130                 135                 140

Leu Leu Asn Gly Lys Trp Ile Leu Ala Tyr Thr Ser Phe Ser Gly Leu
145                 150                 155                 160

Phe Pro Leu Leu Ala Arg Gly Asn Leu Leu Pro Val Arg Val Glu Glu
                165                 170                 175

Ile Ser Gln Thr Ile Asp Ala Glu Thr Leu Thr Val Gln Asn Ser Val
            180                 185                 190

Val Phe Ala Gly Pro Leu Ser Thr Thr Ser Ile Ser Thr Asn Ala Lys
            195                 200                 205

Phe Glu Val Arg Ser Pro Lys Arg Leu Gln Ile Asn Phe Glu Glu Gly
210                 215                 220

Ile Ile Gly Thr Pro Gln Leu Thr Asp Ser Ile Glu Leu Pro Glu Asn
225                 230                 235                 240

Val Glu Phe Leu Gly Gln Lys Ile Asp Leu Ser Pro Phe Lys Gly Leu
                245                 250                 255

Ile Thr Ser Val Gln Asp Thr Ala Thr Ser Val Ala Lys Ser Ile Ser
            260                 265                 270

Ser Gln Pro Pro Ile Lys Phe Pro Ile Ser Asn Ser Tyr Ala Gln Ser
            275                 280                 285
```

```
Trp Leu Leu Thr Thr Tyr Leu Asp Ala Glu Leu Arg Ile Ser Arg Gly
    290                 295                 300

Asp Ala Gly Ser Ile Phe Val Leu Ile Lys Glu Gly Ser Pro Leu Leu
305                 310                 315                 320

Lys Pro

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide
<220> FEATURE:
<223> OTHER INFORMATION: n = inosine

<400> SEQUENCE: 4
ggaattcgan aantayggng anga                                          24

<210> SEQ ID NO 5
<211> LENGTH: 5
<212> TYPE: PRT
<213> ORGANISM: Cucumis sativus

<400> SEQUENCE: 5

Glu Lys Tyr Gly Asp
1               5

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 6
garaattccc aracyatyga t                                             21

<210> SEQ ID NO 7
<211> LENGTH: 7
<212> TYPE: PRT
<213> ORGANISM: Cucumis sativus

<400> SEQUENCE: 7

Glu Ile Ser Gln Thr Ile Asp
1               5

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 8
carytgtggw gttcckatta                                               20

<210> SEQ ID NO 9
<211> LENGTH: 6
<212> TYPE: PRT
<213> ORGANISM: Cucumis sativus

<400> SEQUENCE: 9
```

```
Ile Gly Thr Pro Gln Leu
  1               5

<210> SEQ ID NO 10
<211> LENGTH: 1485
<212> TYPE: DNA
<213> ORGANISM: Cucumis sativus

<400> SEQUENCE: 10
aagctttaca aattagggtt actttattca ttttcatcca ttctctttat tgttaaattt     60
tgtacattta ttcaataata ttatatgttt attacaaatt ctcactttct tattcatacc    120
tattcactca agcctttacc atcttccttt tctatttcaa tactatttct acttcatttt    180
tcacgttttt aacatctttc tttatttctt gtccacttcg tttagggatg cctaatgtcc    240
caaatttcat ctctcgtagt aacacaaaac caatgtaatg ctacttctct ctacatttt     300 aatacaaata aagtgaaaca aaatatctat aaataaacaa atatatatat tttgttagac    360
gctgtctcaa cccatcaatt aaaaatttt gttatatttc tactttacct actaaatttg     420
tttctcatat ttaccttta acccccacaa aaaaaaatta taaaaagaa agaaaaaagc      480 taaaccctat ttaaatagct aactataaga tcttaaaatt atcctcatca gtgtatagtt    540
taattggtta ttaacttata acattatata tctatgacat atactctctc ctagctattt    600 ctcacattt ttaacttaag aaaatagtca taacatagtc taaaattcaa acatccacat    660
gctctaattt gattaacaaa aagttagaaa tatttattta aataaaaaag actaataaat    720
atataaaatg aatgttcata cgcagaccca tttagagatg agtatgcttt cacatgctga    780
gattattttc aaaactaagg ttgtagcaat attaaatcaa taaaattatt ataaataaca    840
aaattaacct gctcgtgttt gctgtatatg ggaggctaca aaataaatta aactaaagat    900
gattatgttt tagacatttt ttctatctgt attagtttat acatattaat tcaggagctg    960
cacaacccaa ttctattttc gttccttggt ggctgggttt ctcacaaggt tcaatagtca   1020
atattaggtt ttattggact tttaatagta tcaaacaaat ctatgtgtga acttaaaaat   1080
tgtattaaat atttagggta acctgttgcc gtttttagaa taatgtttct tcttaataca   1140
cgaaagcgta ttgtgtattc attcatttgg cgcctcacat gcttcggttg gctcgcttta   1200
gtctctgcct tctttgtata ttgtactccc cctcttccta tgccacgtgt tctgagctta   1260
acaagccacg ttgcgtgcca ttgccaaaca agtcatttta acttcacaag gtccgatttg   1320
acctccaaaa caacgacaag tttccgaaca gtcgcgaaga tcaagggtat aatcgtcttt   1380
ttgaattcta tttctctttta tttaatagtc cctctcgtgt gatagttttt aaaagatttt   1440
taaaacgtag ctgctgttta agtaaatccc agtccttcag tttgt                   1485
```

US 6,551,793 B1

CAROTENOID-ASSOCIATED PROTEINS USEFUL FOR HIGH CAROTENOID ACCUMULATION AND PRODUCTION IN PLANTS AND OTHER ORGANISMS

This application is a continuation of PCT International Application No. PCT/IL97/00399, filed Dec. 4, 1997 claiming priority of U.S. Provisional Application No. 60/032,421, filed Dec. 5, 1996, now abandoned the contents of which are hereby incorporated in their entireties into the present application.

BACKGROUND OF THE INVENTION

1. Field of Invention

This invention concerns a method for production of high amounts of carotenoids in plants. In particular, the invention concerns carotenoid-associated proteins CHRC and CHRD isolated from corollas of *Cucumis sativus*, CHRC deduced sequence, the molecular cloning, cDNA, RNA and a homologous gene involved in expression of CHRC. The *Cucumis sativus* corollas proteins were found to be involved and to regulate carotenoid accumulation and sequestration in chromplasts. Invention additionally concerns a new CHRC promoter able to direct expression of foreign genes. The cloned promoter comprises approximately 3.5 kb of the CHRC upstream region.

2. Background Art and Related Art Disclosures

Carotenoids are very important dietary components in animals and are also important for plants as they are essential for plant photosynthesis. In humans, they are essential dietary components, which possess anticancer activity and protect against heart and age related diseases. Commercially, they are used-to color food products. In flowers and plants they are responsible for their pigmentation. In photosynthetically active organisms, carotenoids are essential to the proper functioning of the light-harvesting apparatus and they determine color of fruits and flowers. Moreover, carotenoid synthetic pathway leads to the synthesis of key growth regulators.

In plants, carotenoids are accumulated in high amounts chromoplasts, that are carotenoid-containing plastids responsible for the yellow, orange and red colors of petals, fruits and some roots in various plant species. Information on the structural organization of chromoplasts comes mainly from studies of ripening processes in fruits [Plant Sci. 94:1–17 (1983)]. The disappearance of chlorophyll and accumulation of carotenoids have been shown to parallel fruit maturation. Following the chloroplast to chromoplast conversion thylakoid membranes disintegrate, most of the components of the photosynthetic machine disappear, and a new set of proteins accumulates instead. In pepper fruits containing fibrillar chromoplasts, two very abundant proteins with approximate molecular masses of 35 kDa (ChrB) and 58 kDa (ChrA) have been identified as chromoplast-specific [Plant Mol. Biol. 21:549–554 (1993)]. When their pattern of expression was studied, the former was found to accumulate early and remain throughout ripening, whereas the latter appeared only at the final stage of fruit-color development and was found to be a carotenoid-associated protein [Plant Physiology 91:455–458 (1989)].

Identification of the protein fibrillin in bell peppers as an essential structure component of chromoplast-specific, carotenoid-accumulating lipoprotein structures, termed fibrils, and the isolation of its cDNA and genomic clones were very important steps towards understanding the internal structure of chromoplasts [Plant Cell 6:119–133 (1994)]. Analysis of this gene's expression in bell pepper revealed that both the protein and the transcript accumulate in parallel to fruit ripening. The bell pepper clone, however, did not reveal homologous transcripts in other tissues or plants, ibid.

To date, a number of genes from the carotenoid biosynthetic pathway in fruits have been cloned [Plant Mol. Biol. 27:425–428 (1995); Plant Mol. Biol. 27:1153–1162 (1995)]. Of these, however, only one, encoding capsanthin-capsorubin synthase [Plant Cell 7:1027–1038 (1995); Plant J. 6:45–54 (1994); Curr. Genet. 26:524–527 (1994)], shows fruit-chromroplast-specific expression.

Flower pigmentation due to carotenoid accumulation has also been studied. In *Tropaeolum majus* corollas, a 30 kDa protein accumulated in parallel to flower development and appeared to be a major and obligatory component of chromoplast fibrils [Protoplasma 157:128–135 (1990)]. Proteins of 30 and 68 kDa were characterized as the main proteins of *Viola tricolor* chromoplast globules [Plant Cell Res. 1:111–114 (1982)]. In nasturtium flowers, an immunocomplex band of 32 kDa was revealed with fibrillin antibodies [Plant Cell 6:119–133 (1994)]. With respect to genes of the carotenoid biosynthetic pathway, expression of phytoene synthase (PSY) and phytoene desaturase (PDS) in tomato flowers was shown to peak just before anthesis [Plant Cell 5:379–384 (1993)]. The petals and anthers of mature flowers accumulated the highest levels of these transcripts, as compared with other organs. Nevertheless, expression of both PSY and PDS was found not to be flower-specific.

Young green flower buds of *Cucumis sativus* contain chloroplasts, which are converted to fibrillar chromoplasts as the flower matures. Only chromoplasts are found in the mature yellow corollas [Physiol. Plant 104:321–326 (1994)]. An isolated 35 kDa chromoplast-specific protein (CHRC) from cucumber corollas was shown to be associated with carotenoids. While the above-findings are interesting from the botanical point of view, they do not have a practical utility.

Since carotenoids are so important for both plants and animals it would be of a great advantage to utilize in some way the above findings to achieve and control a higher production or accumulation of carotenoids in plants or cells, or their easy production by bacterial cells.

It is, therefore a primary object of this invention to provide a method for genetic control of production and/or accumulation of high levels of carotenoids in cells of plants, bacteria or other organisms.

SUMMARY

One aspect of the current invention is a method for production, accumulation and sequestration of high amounts of carotenoids in plant, bacteria or other cells by molecular and other type manipulations of carotenoid-associated proteins.

Another aspect of the current invention is a gene of which expression produces a protein which controls and is involved in a production, accumulation and sequestration of carotenoids in plant, bacteria or other cells.

Another aspect of the current invention is a method for molecular cloning of chrc gene encoding for the carotenoid-associated protein CHRC from *Cucumis sativus*.

Still another aspect of the current invention is a gene containing domain which is homologous to domains present in a variety of chromoplasts containing plants.

Still another aspect of the current invention is a nucleotide sequence (SEQ ID NO:1) of the chrc gene encoding the *Cucumis sativus* protein CHRC.

Still another aspect of the current invention is an amino acid sequence (SEQ ID NO:2) comprising 322 amino acid of the CHRC protein of *Cucumis sativus*.

Still yet another aspect of the current invention is a partly sequenced CHRC promoter having a nucleotide sequence (SEQ ID NO:10).

Another aspect of the current invention is a method for high production of carotenoids using bacterial cells having introduced CHRC gene intracellularly together with genes encoding enzymes for carotenoid biosynthesis.

DEFINITIONS

As used herein:

"CHRC" means chromoplast-specific carotenoid-associated protein.

"CHRD" means a minor chromoplast-specific protein of about 14 kD isolated from cucumber corolla chromoplasts.

"Anthesis" means the flowering period in flowers and plants.

"Corolla" means collectively the petals and flowers.

"Thylakoid" means a membranous lamella of protein and lipid implant chloroplasts where the photochemical reactions of photosynthesis take place.

"Gibberellins" or "GA" means plant hormones that regulate various aspects of plant growth and development, such as germination, cell growth, stem elongation, flower and fruit development and pigmentation.

"Gibberellin $A_3$" or "$GA_3$" means a hormone which up-regulates production of CHRC protein expression.

DETAILED DESCRIPTION OF THE INVENTION

Figure 1A:
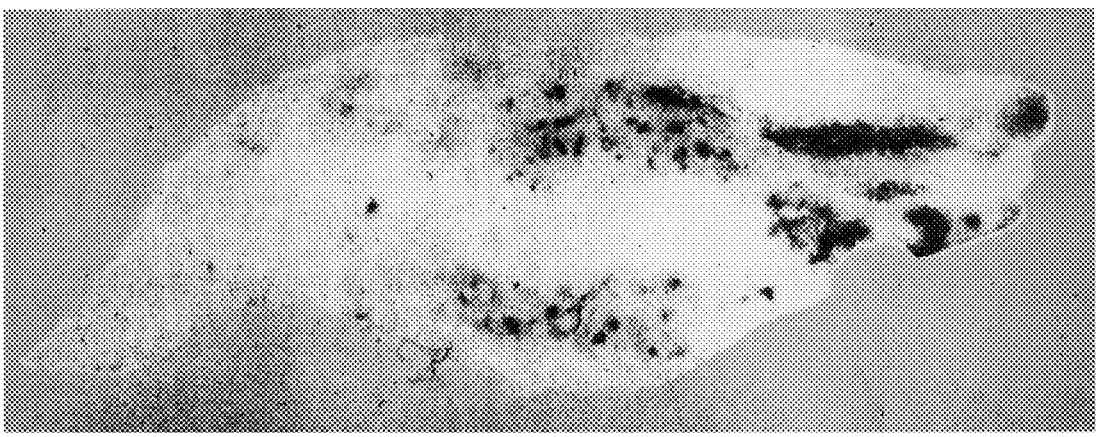
FIGS. 1A and 1B show comparative photographs of cucumber flowers petals showing transient expression of the reporter gene GUS using CHRC promoter (FIG. 1A) or known 35S CaMV promoter (FIG. 1B).
Figure 1B:
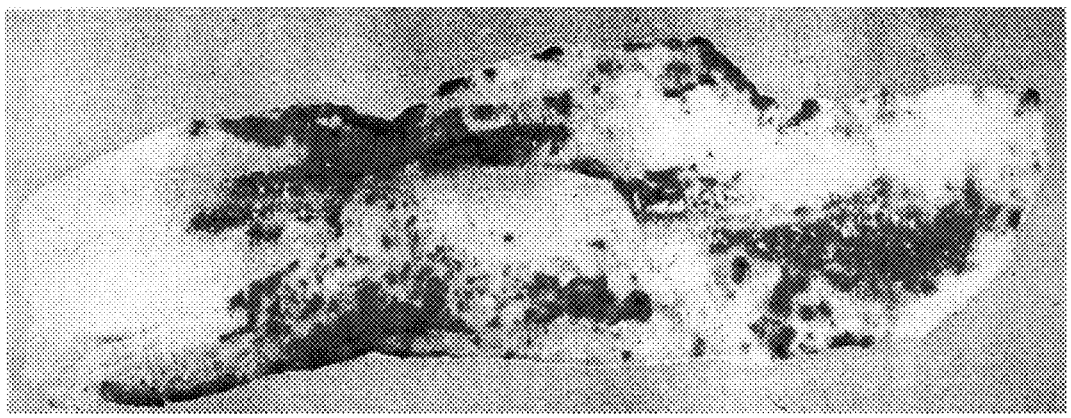

This invention concerns proteins and genes involved in carotenoids accumulation, sequestration and production in non-photosynthetic tissues of plants, bacteria or in other cells. The invention discloses a genetic manipulation of certain plants through upregulation of expression resulting in increased production of carotenoid-associated proteins which cause increased accumulation and sequestration of carotenoids in chromoplasts.

Chromoplasts are carotenoid-accumulating plastids found in the corollas and fruits of many higher plants. In most cases, the pigment in these plastids is accumulated with the aid of carotenoid-associated proteins located within unique structures. The invention discovered a method for genetic manipulation of carotenoid accumulation of plastids by providing means for increased production of carotenoid-associated proteins.

I. chrc Gene and CHRC Protein Encoded by It

The current invention concerns discovery of the existence of a group of homologous genes coding for chromoplast-specific, carotenbid-associated proteins involved in carotenoid production and accumulation in various plants.

This invention discloses the isolation and characterization of the cDNA of the CHRC gene from *Cucumis sativus* corollas which encodes the chromoplast-specific carotenoid-associated proteins CHRC. The transit peptide cleavage site was determined and, using a chloroplast uptake system, it was shown that CHRC can be post-translationally targeted to these plastids where they are peripherally associated with thylakoids. Analysis of CHRC transcript level in *Cucumis sativus* revealedits temporal and tissue-specific regulation: the transcript was detected only in corollas, where its level increased in parallel to flower development, peaking just before anthesis.

Immunological analysis of CHRC expression revealed it to be regulated in a temporal and tissue-specific manner. The steady-state levels of CHRC increased in parallel to cucumber flower development and carotenoid accumulation, peaked right before anthesis, dropped to a very low level only 24 hours after anthesis and was undetectable in leaves. Antibodies against CHRC and CHRD also cross-reacted with proteins of approximately 35 kDa in corollas of other representatives of the Cucurbitaceae family, such as squash, melon and watermelon. Results of studies of the effect of hormones on CHRC and carotenoid accumulation shows that gibberellin $A_3$ ($GA_3$) is intimately involved in regulation of chromoplast biogenesis in corollas.

CHRC shares significant homology (59%) with the gene coding for fibrillin. Fibrillin is a protein found in *Capsicum annum* red pepper whose function is essentially identical to that of CHRC. A CHRC fragment, including the potential active site of the protein, was used as a probe in Northern blot analyses of floral and fruit tissues from various plants containing chromoplasts of different types. CHRC homologs of similar sizes were revealed in all cases. The existence of a group of homologous genes coding for chromoplast-specific proteins which aid in the sequestration of carotenoids with specific structures seems evident from these findings.

The detection of expression of CHRC counterparts in other fibrinous chromoplast-containing plants, and even in plants with crystallous and globulous-type chromoplasts such as tomato and orange fruits suggests the existence of a homologous group of genes coding for apoproteins which aid in carotenoid sequestration within chromoplasts. The level of homology within the group, based on the homology between CHRC and fibrillin, is similar to that between genes coding for enzymes of the carotenoid biosynthetic pathway, such as PSY and PDS.

A. CHRC Gene and Isolation of CHRC cDNA

The present invention additionally concerns the isolation and characterization of the *Cucumis sativus* gene (CHRC) encoding a corolla-chromoplast-specific, carotenoid-associated protein. *Cucumis sativus* gene (CHRC) was isolated and characterized. The gene has been deposited under Access Number: X95593 on Feb. 8, 1996 at the EMBL/Gen Bank/DDBS databases. Nucleotide and deduced amino acid sequences of CHRC cDNA are seen in Table 1.

The post-translational targeting of this nuclear-encoded protein to plastids, and the cleavage site of the transit peptide were demonstrated. Based on the expression pattern of this gene in cucumber tissues and of its homologs in chromoplastogenic organs of a number of other plants, the existence of a group of homologous genes coding for chromoplast-specific, carotenoid-associated proteins is proposed.

Two degenerate primers, N and R, synthesized according to the N-terminal and internal amino acid microsequences of CHRC, respectively, were used to amplify cucumber corolla (stage 3, 24 hours before anthesis) cDNA. When the resultant PCR product of 443 bp was used as a probe in Northern blot analyses, corolla-tissue-specific signal was revealed. Moreover, when used as a template for PCR with F (an oligonucleotide synthesized according to the internal amino acid sequence) and R primers, an approximately 160 bp product was generated. The 443 bp DNA fragment was cloned and sequenced. The predicted amino acid sequence of the cloned DNA fragment exhibited a 100% match to the three available microsequences of CHRC.

To isolate cDNA encoding the entire CHRC, a corolla cDNA library was constructed and screened with the cloned DNA fragment. The largest insert contained in one of the positive clones was fully sequenced. This cDNA, termed CHRC, contained a region with a sequence identical to that yielded by PCR. The CHRC cDNA is seen in SEQ ID NO:1 and in Table 1. Table 1 shows nucleotide sequence (SEQ ID NO:1) of CHRC gene and predicted amino acid sequence (SEQ ID NO:2) of its expressed carotenoid-associated CHRC protein. Nucleotide sequence consists of 74 bp 5'-untranslated region, a 966 bp open reading frame, a stop codon and a 293 bp 3'-untranslated region including a 27 bp poly(A) tail. The N-terminal and two internal peptide microsequences are underlined. The sequence of the PCR-generated 443 bp product is in bold face. The arrowhead indicates the cleavage site of the transit peptide and the translation terminal codon is marked with an asterisk. The CHRC precursor protein, based on the derived sequence of 322 amino acids, had a predicted molecular mass of 35.2 kDa and consisted of two parts: a 58 amino-acid-long transit peptide and a mature protein (264 amino acids) with a predicted molecular mass of 29.3 kDa. Based on its mobility on an SDS-PAGE, the molecular mass of-the mature CHRC was estimated at 35 kDa. Furthermore, expression in *Escherichia coli* yielded an approximately 41 kDa protein that cross-reacted with CHRC antisera (not shown). The cleavage point of the precursor protein (between amino acids R and A) (FIG. 1*a*) was determined based on the N-terminal microsequence of the mature CHRC.

TABLE 1

Nucleotide and Predicted Amino Acid Sequences

```
AGTAAATCCC AGTCCTTCAG TTTGTGCTTT TGTGTGTTTT GTTTCTCTGA TTTACGGAAT    60
TTGGAAATAA TTCTATGGCG TTTGTTTCTA AATTCAATCA ACTTCCGTGC AAGACTCTCG   120
                M    A    F    V    S    Q    F    N    Q    L    P    C    K    T    L    A      16
CACTCAATCC ACCACAACCT CAATTGACTT CTAAGCCTTC GGTTTTCCCC ATCGCTTCGA   180
L    N    P    P    Q    P    Q    L    T    S    K    P    S    V    F    P    I    A    S    I      36
TTGGGGCTAC CGCCAGAGCC GCGGCGGGGA AGTCACTGAT CTCAGTTAGG CCTGCGTTCA   240
G    A    T    A    R    A    A    G    K    S    L    I    S    V    R    P    A    F    K      56
AGGTCCGTGC GGTGTTAAAC GATGACGAGT GGGGGGAGGA TAAGGATGAG AAGTATGGAG   300
V    R ↓  A    V    L    N    D    D    E    W    G    E    D    K    D    E    K    Y    G    D      76
ATGATTCGTC TGTGGCGGTA GCTGAAAAGG AGGAGGAAAA GCCTCTGGAG CCATCCGAGA   360
D    S    S    V    A    V    A    E    K    E    E    E    K    P    L    E    P    S    E    I      96
TTTATAAACT GAAGAAGGCG TTGGTGGACT CGTTTTACTT GACCGATCGT GGATTACGAG   420
Y    K    L    K    K    A    L    V    D    S    F    Y    G    T    D    R    G    L    R    V     116
TGTCCAGAGA TACTAGGGCG GAGATTGTCG AGCTGATTAC GCAACTGGAA TCGAAGAACC   480
S    R    D    T    R    A    E    I    V    E    L    I    T    Q    L    E    S    K    N    P     136
CAACCCCTGC TCCTACTGAG GCCCTGACTC TGCTCAACGG CAAGTGGATT CTAGCGTACA   540
T    P    A    P    T    E    A    L    T    L    L    N    G    K    W    I    L    A    Y    T     156
CAACTTTCGC GGGTCTGTTC CCGTTGTTGT CTAGGAATTT GCCATTGGTC AAAGTGGAGG   600
T    F    A    G    L    F    P    L    L    S    R    N    L    P    L    V    K    V    E    E     176
AAATTTCACA GACAATTGAT TCAGAGAAVV TCACCGTCCA AAACTCTGTC CAGTTTTCCG   680
I    S    Q    T    I    D    S    E    N    L    T    V    Q    N    S    V    Q    F    S    G     196
GTCCTCTAGC CACCACTTCC ATTACTACCA ATGCAAAGTT TGAAGTTCGA AGTCCCCTGC   720
P    L    A    T    T    S    I    T    T    N    A    K    F    E    V    R    S    P    L    R     216
GTGTACATAT CAAATTCGAA GAAGGTGTCA TTGGAACTCC CCAGCTGACG GATTCGATAG   780
V    H    I    K    F    E    E    G    V    I    G    T    P    O    L    T    D    S    I    V     236
TGATACCAGA TAATGTGGAC TTTCTTGGGC AGAAGATTGA CTTTACACCA TTCAATGGTA   840
L    P    D    N    V    D    F    L    G    Q    K    I    D    F    T    P    F    N    G    I     256
TCATATCTTC CCTTCAAGAC ACTGCTTCAA ATGTAGCCAA GACGATTTCG AGTCAACCAC   900
I    S    S    L    Q    D    T    A    S    N    V    A    K    T    I    S    S    Q    P    P     276
CAATCAAGTT CTCAATCTCA AACACGAGGG TAGAGTCTTG GTTGCTAACT ACTTATCTTG   960
I    K    F    S    I    S    N    T    R    V    E    S    W    L    L    T    T    Y    L    D     296
ATGAAGATCT TCGAATTTCA CGAGGAGATG GTGGTAGCGT GTTCGTACTC CTCAAGGAAG  1020
```

TABLE 1-continued

Nucleotide and Predicted Amino Acid Sequences

| E | D | L | R | | I | S | R | | G | D | G | | G | S | V | F | | V | L | L | | K | E | G | | 316 |
|---|---|---|---|---|---|---|---|---|---|---|---|---|---|---|---|---|---|---|---|---|---|---|---|---|---|-----|

```
GCAGTTCTTT CTTGTCTCTC TAAACACCCT TACTCTTCTC ACTATAAAGG GTTCATAGGA    1080
S  S  F  L    S  L  *                                                322
AACTGAATTA TTATTCAAGG ATGTTTTTAA ACGTGTTGTA GTTTCTTATC AAATAGTGAA    1140
TGATATTGCC TTCTGTTCAA AGGGCCAGCT TCAATTAGCT TCATCTTCTT TTAAATCACT    1200
AGTTACTTGA ATTTCTGTTG AGAAAATAAA CATTGTTTAT ATTTTACCCA TACTGTACCA    1260
AAAGCCAAAA GTTAAACCAA AACGTGTGAA AAGCTTGGAA GGGCTTGAC polyA          1309
```

SEQ ID NO:1 of 1309 nucleotides, seen in Table 1, is a cDNA sequence of the chrc gene. Fragments and variants thereof are domains comprising nucleotides 309–379, 663–705 or 803–831. These fragments and their variants are intended to be within the scope of the invention.

SEQ ID NO:2 of 322 amino acids, seen in Table 1, is an amino acid sequence of CHRC protein. Fragments and variants thereof are domains comprising amino acids 59–82, 177–191 and 224–233. These fragments and their variants are intended to be within the scope of this invention.

Figure 2:
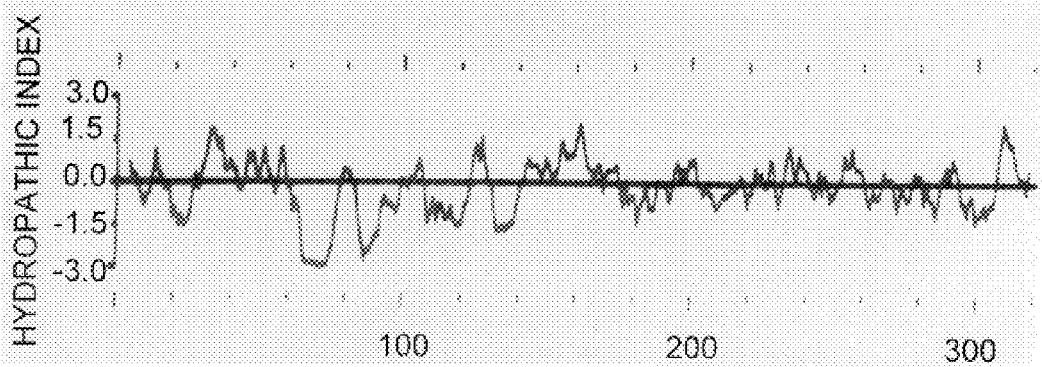
FIG. 2 shows a hydropathy plot of the predicted CHRC amino acid sequence determined according to Kyle and Doolittle [supra.] using a window size of eight amino acids.

FIG. 2 shows a hydropathy plot of the predicted amino acid sequence determined according the Kyte and Doolittle [J. Mol. Biol. 157:105–132 (1982)] using a window size of eight amino acids. Increased hydrophobicity is indicated by positive values. The hydropathy plot showed hydrophobic regions in the C-terminal portion of the transit peptide and in the middle and C-terminal portions of the mature protein. The most hydrophilic region was situated in the N-terminal portion of the mature protein. The predicted p1 of the mature CHRC was 4.9, whereas that of the CHRC transit peptide was 12.3.

CHRC SVRPAFKVR1AVLNDDEWGEDKDEKYGDDSS VAVAEKEEEKPLEPSEIYKL

The cucumber CHRC cDNA clone isolated and characterized in the present invention shared no significant homology with previously published sequences available in GeneBank, aside from that of fibrillin. The two proteins of similar molecular mass shared a number of common features: a positively charged transit peptide, acidic p1 of the mature protein, a similar three-dimensional structure based on hydropathy profiles, a lack of cysteine residues, tandem glutamic/aspartic acid residues, identical 7 and 25 amino acid domains in transit and mature peptides, respectively, a probably helical transmembrane region which is 90% identical, and a cell adhesion motif. Table 2 compares amino acid sequences of CHRC and fibrillin, a carotenoid-associated protein from red peppers. As seen in Table 2, CHRC and fibrillin from pepper fruits shared 59% homology at the DNA level, and 64% identity/74% similarity at the amino acid level. Comparison of CHRC and fibrillin amino acid sequences, seen in Table 2 shows the highly conserved regions in the transit peptide (8–15) and in the mature protein (120–144) are underlined. Amino acids in italicized bold face indicate the probably helical transmembrane region (147–164). The arrow indicates the cleavage site of the transit peptide. The potential cell adhesion motif is double-underlined. The longest region in CHRC exhibiting 100% identity with the corresponding region in fibrillin spanned residues 120–144. Despite their low level of homology (32% identity/48% similarity), transit peptides of CHRC and fibrillin shared a common domain of seven amino acids. Similar to fibrillin, the mature CHRC did not contain any cysteine residues, and had several tandem aspartic and/or glutamic acid residues at positions 63–65, 68–69, 71–72, 86–88, 176–177 and 222–223. A highly probably helical transmembrane region was detected for amino acids 147–164 in both CHRC and fibrillin. The two sequences also shared the potential cell adhesion motif RGD as described in Trends Biol. Sci. 16:246–260 (1991) at position 303. This high level of similarity between CHRC and fibrillin reflects their similar structural role in fibrillous-type chromoplasts, irrespective of organ or plant type.

B. In vitro Transcription/Translation and Targeting to Chloroplasts

Figure 3A:
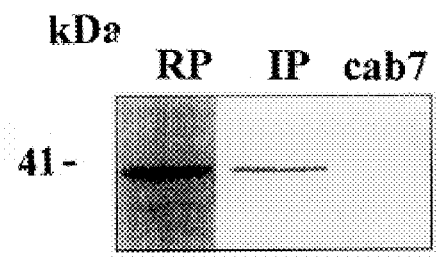
FIGS. 3A and 3B show in vitro transcription/translation of CHRC and import into intact chloroplasts.
Figure 3B:
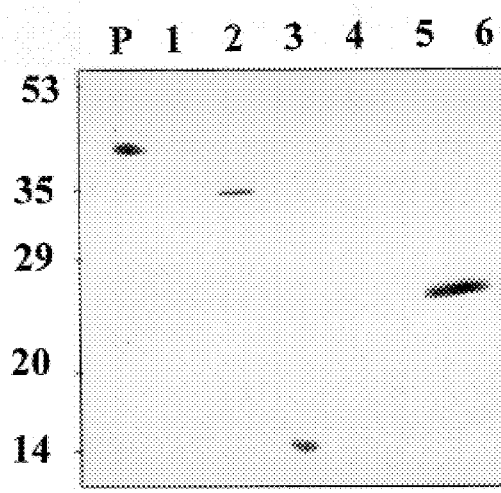

In vitro transcription/translation of CHRC and import into intact chloroplasts is seen in FIG. 3. In FIG. 3A, the CHRC cDNA was transcribed and translated in vitro and the radio-labeled product (RP) was analyzed by SDS-PAGE followed by fluorography. Immunological blotting of the CHRC translation product (IP) and of Cab7 (Cab7) as a control was performed using antibodies against CHRC. FIG. 3B shows SDS-PAGE and fluorography of stromal (lanes 1, 3 and 5) and thylakoid (lanes 2, 4 and 6) subfractions obtained from thermolysin-treated chloroplasts following import of radio-labeled CHRC (lanes 1 and 2), SSU (lanes 3 and 4) and Cab7 (lanes 5 and 6) precursors. Radio-labeled CHRC precursor is shown in lane P. Molecular mass markers are indicated on the left.

In vitro transcription/translation of the CHRC cDNA clone yield a 41 kDa radio-labeled product that cross-reacted with CHRC-specific antibodies as seen in FIG. 3A. When the radio-labeled CHRC precursor was incubated with intact chloroplasts, followed by treatment with thermolysin, only the processed CHRC, having a mobility consistent with that of authentic mature CHRC, was revealed. Following chloroplast fractionation, as seen in FIG. 3B, the processed CHRC was found to be associated with thylakoids and was not observed in the stromal fraction.

Parallel uptake experiments with chloroplast-specific radio-labeled chlorophyll a/b binding protein (Cab7) and the small subunit (SSU) of Rubisco revealed the following results. The processed Cab7 was found in the thylakoids, whereas SSU was observed in the stromal fraction. To characterize the association between the imported CHRC and the thylakoids, the isolated membranes were treated with either NaOH or thermolysin for 30 minutes. Following either of these treatments, the protein did not remain associated with the membranes and was only revealed in the NaOH-wash fraction (data not shown), suggesting that when present in chloroplasts, it is peripherally associated with thylakoid membranes.

C. Expression of CHRC mRNA

The expression pattern of CHRC at the RNA level was regulated in a temporal and tissue-specific manner. A very similar pattern of expression has been revealed for CHRC at the protein level. Using an in vitro flower bud culture system that mimics in vivo flower development, CHRC mRNA levels in corollas were shown to be specifically up-regulated by gibberellic acid. The patterns of CHRC up-regulation by GA$_3$ and down-regulation by abscisic acid and ethylene were observed to be essentially identical at both and protein and RNA levels.

Figure 4:
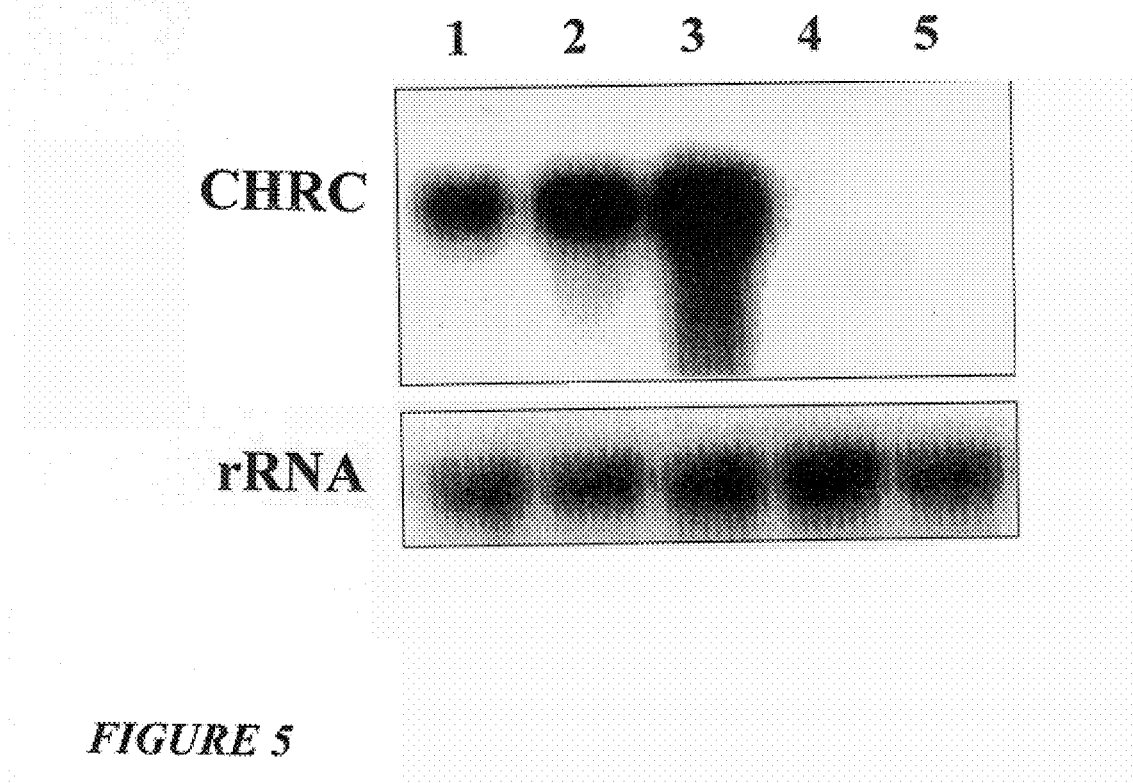
FIG. 4 is a Northern blot analysis of CHRC expression during cucumber flower development.
Figure 5:
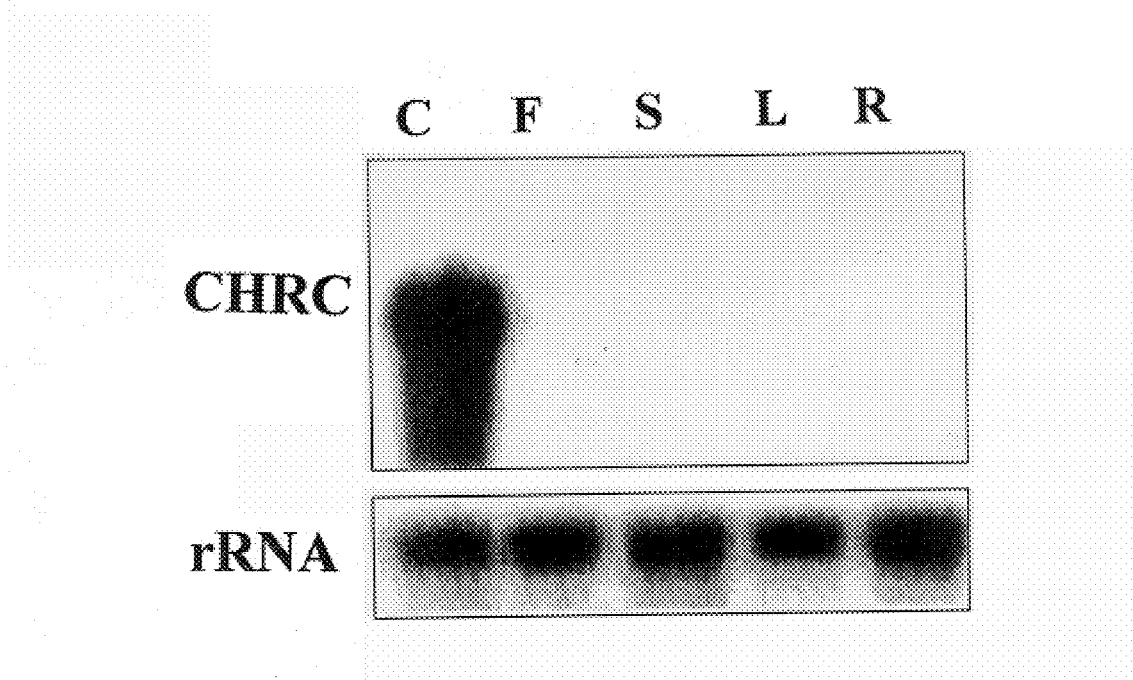
FIG. 5 is a Northern blot analysis of CHRC mRNA in different cucumber tissues.

FIGS. 4–6 show temporal and tissue-specific regulation of CHRC transcript in corollas.

FIG. 4 is Northern blot analysis of CHRC expression during cucumber flower development. In FIG. 4, total RNA extracted from cucumber flower corollas at stages 1–5 (lanes 1–5) was probed with radio-labeled CHRC cDNA. The same RNA blot was rehybridized with 18S ribosomal RNA probe (rRNA). Stage 1 corollas were green and contained chloroplasts, whereas filly developed corollas at anthesis (stage 4) were yellow and contained only chromoplasts. In parallel to flower development, the level of CHRC RNA, approximately 1.3 kb, increased up to stage 3, that is 24 hours before anthesis. It could be barely detected at anthesis and was undetectable in stage 5 corollas, that is 24 hours after anthesis.

FIG. 5 shows results of Northern blot analysis of CHRC mRNA in different cucumber tissues. In FIG. 5, total RNA extracted from cucumber corollas (C), fruits (F), stems (S), leaves (L) and roots (R) was probed with radiolabeled CHRC cDNA. The same RNA blot was rehybridized with 18S ribosomal RNA probe (rRNA).

As seen in FIG. 5, the analysis of CHRC expression in various cucumber tissues revealed a high level of CHRC transcript in the RNA from corollas, whereas transcript could not be detected in the other tissues analyzed, even under low-stringency hybridization conditions.

To study whether CHRC has counterparts in chromoplast-containing tissues of other plants, Northern blot analysis was performed with RNA extracted from fruits and corollas of various plant species.

Figure 6A:
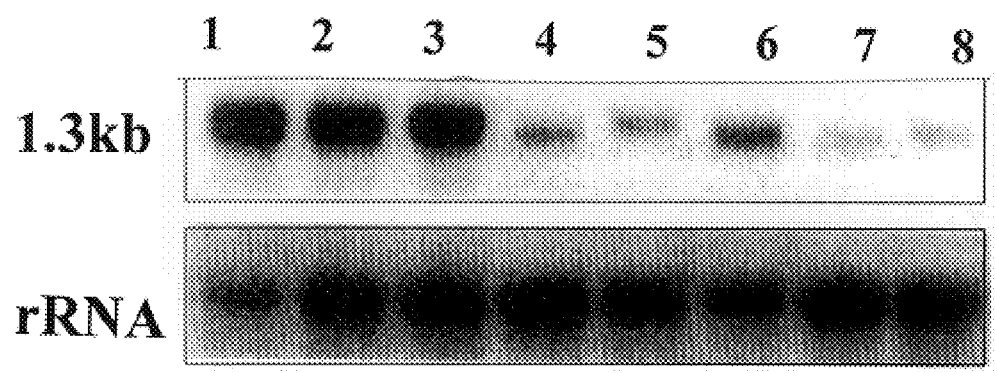
FIGS. 6A and 6B are Northern and Western blot analyses of chromoplast-containing tissues from different plants.

FIG. 6 shows results of Northern and Western blot analyses of chromoplast-containing tissues from different plants. In FIG. 6, total RNA (a) and total protein (b) were extracted from cucumber (1), melon (2) and watermelon (3) corollas, pepper fruits (4), Heleniutn (5) and tomato (6) corollas, tomato fruits (7) and orange peels (8). The RNA blot was probed with a CHRC cDNA fragment (480–765). The same RNA blot was rehybridized with 18S ribosomal RNA probe (rRNA). Northern blot analysis is shown in FIG. 6A. Using CHRC as a probe, a strong hybridization signal was revealed in the corollas of melon (*Cucumis melo* L.) and watermelon (*Citrullus vulgaris* Schrad.), both of which contain fibrillar chromoplasts. The transcript size in these plants, which belong to the Cucurbitaceae family along with the cucumber, was identical to that of the cucumber CHRC RNA. Much weaker signals of a slightly different size were observed in red bell pepper fruits (*Capsicum annum* L.) and in yellow corollas of *Helenium autumnale* L. No hybridization signal was revealed with RNA from orange peels (*Citrus sinensis* L.), or from tomato corollas or fruits (*Lycopersicon esculentum* L.) (data not shown). On the other hand, when a CHRC fragment (480–765) which is highly homologous to fibrillin (85% similarity) was used as a probe, the hybridization signal was also seen in tomato corollas and red fruits, and in orange peels. This fragment includes the potentially active sites of CHRC, comprising surface loops and a trans-membrane helix, but does not include regions of low homology such as that coding for transit peptide, and the 5' and 3' untranslated regions.

Figure 6B:
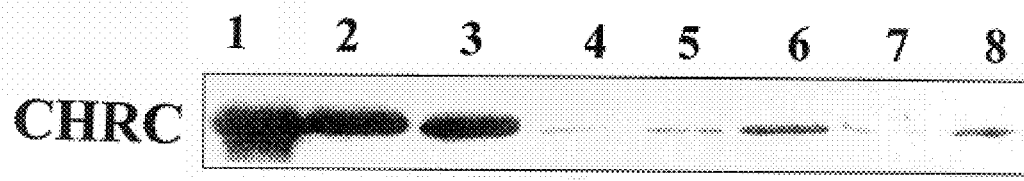
Figure 7A:
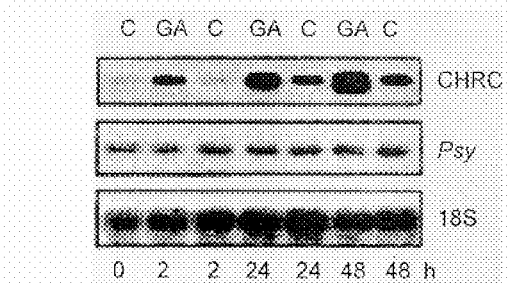
FIGS. 7A and 7B show kinetics of CHRC mRNA and protein accumulation in response to $GA_3$.
Figure 7A:
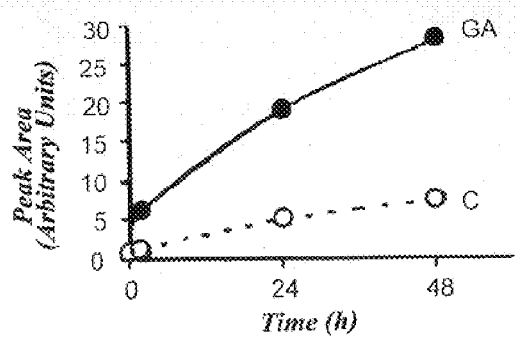
Figure 7B:
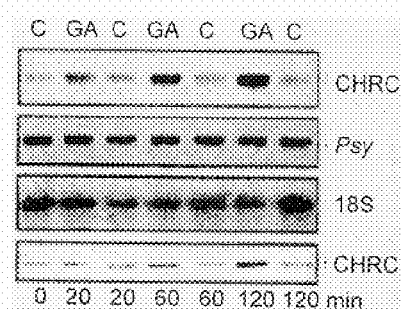
Figure 7B:
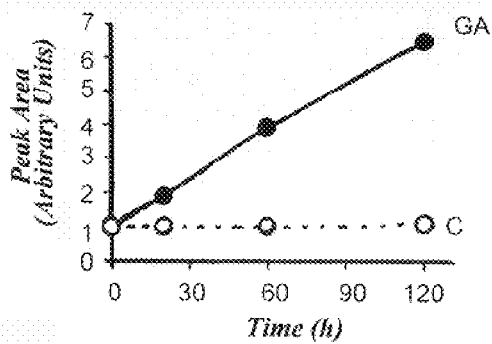

Western blot analysis, as seen in FIG. 6B, was performed using antibodies against CHRC protein. Using a sensitive ECL detection system immuno-complex bands with a mobility of approximately 35 kDa was revealed.

Based on the above findings, genes for carotenoid synthesis and accumulation were shown to be strongly regulated at the transcriptional level.

D. GA$_3$ Involvement in Up-Regulation of CHRC Synthesis

Gibberellins (GAs) are plant hormones that regulate various aspects of plant growth and development, such as germination, cell growth, stem elongation, flower and fruit development, and pigmentation.

The involvement of GAs in various aspects of cucumber (*Cucumis sativus* L.) floral organ development is well documented. The involvement of a specific hormone GA$_3$ in chromoplast biogenesis in corollas was characterized. Two chromoplast-specific carotenoid-associated proteins (CHRC and CHRD) were identified and shown to be specifically up-regulated by GA$_3$. The effect of antagonists and inhibitors of GA$_3$, such as abscisic acid and paclobutrazol, and an inhibitor of protein synthesis, such as cycloheximide, were studied and their effect on GA$_3$ upregulation of CHRC synthesis was determined.

An in vitro flower bud culture system, previously shown to mimic in vivo flower development was used to study the effect of GA$_3$ on CHRC expression. Isolation and characterization of a single-copy gene coding for CHRC allowed determination of GA regulatory function of carotenoid-associated proteins.

Figure 8:
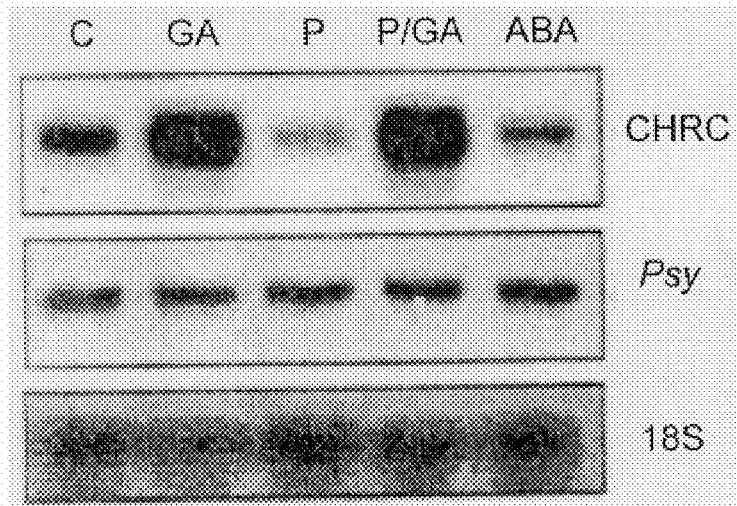
FIG. 8 shows effects of paclobutrazol and ABA on CHRC mRNA level.

Results of the studies involving the effect of GA$_3$ is seen in FIGS. 7 and 8.

FIG. 7 shows kinetics of CHRC mRNA and protein accumulation in response to GA$_3$. Young flower buds were cultured in vitro in the presence (GA) or the absence (C) of 100 μM GA$_3$ for up to 48 hours. Northern and Western blot analyses of corollas, cultured for the indicated periods of time, were performed. The Northern blots (25 μg total RNA/lane) were hybridized with $^{32}$P-labeled DNA inserts from CHRC (CHRC), MEL6 (Psy), and 18s rDNA (18S). Western blot analysis (bottom panel of A) was performed using antibodies against CHRC protein (25 μg total protein/lane). The results of the CHRC Northern blot analyses are also shown graphically relative to the mRNA level of the untreated corollas at zero time (0) (arbitrary value of 1).

As seen in FIG. 7, CHRC mRNA level was very rapidly affected by exogenous GA$_3$ (FIG. 7A); after 20 minutes of treatment, it was approximately twice as high in treated versus control corollas. With longer incubation periods, the level of CHRC mRNA in GA$_3$-treated corollas increased further, to approximately 5- or 6-fold that of untreated control corollas. A closer examination of early time points revealed a detectable increase in CHRC mRNA level within 10–20 minutes in response to GA$_3$ (data not shown). At the protein level, the effect of GA$_3$ on CHRC was slower; after 2 hours of treatment, approximately 2.5 times more CHRC per unit of protein had accumulated in treated versus control corollas (FIG. 7A). No change in the total protein content of corollas was detected within 6 hours of treatment. To determine whether GA$_3$ also affects the expression of genes encoding enzymes from the carotenoid biosynthesis pathway, the expression of Psy, the first committed gene of that pathway, was studied. Psy mRNA levels were rather stable during the first 45 hours of corollas development and were not affected by GA$_3$ treatment.

To further characterize the involvement of GAs in CHRC expression, the effect of paclobutrazol, an inhibitor of GA synthesis, on CHRC mRNA levels was analyzed. Results are seen in FIG. 8.

FIG. 8 shows effects of paclobutrazol and ABA on CHRC mRNA level. Flower buds were cultured in the presence of 100 μm GA$_3$ (GA), 100 μg/ml paclobutrazol following 2 hours of pretreatment with 100 μg/ml paclobutrazol (P), 100 μg/ml paclobutrazol +100 μm GA$_3$ following 2 hours of pretreatment with 100 μg/ml paclobutrazol (P/GA), 100 μM ABA (ABA), or no phytohormones (C). Total RNA was extracted from corollas after 2 hours of treatment. Northern blot analyses were performed and probed as described in the legend to FIG. 7.

As seen in FIG. 8, the addition of paclobutrazol to the in vitro bud culture system led to a 4-fold decrease in CHRC mRNA levels relative to control untreated corollas. Inclusion of exogenous $GA_3$ in addition to paclobutrazol not only prevented the down-regulation, it up-regulated CHRC transcript accumulation to the level of $GA_3$-treated corollas.

ABA antagonizes GA in many developmental processes and has been shown to have an inhibitor, effect on CHRC protein accumulation. To obtain additional support for the role of $GA_3$ in the regulation of CHRC expression, the effect of ABA on CHRC transcript accumulation was analyzed. When 100 $\mu$M ABA was added to the in vitro bud culture system, the CHRC mRNA level was down-regulated 2.5 times as compared with control corollas. The inhibitory effect of ABA on CHRC transcript accumulation was concentration-dependent. Application of 10 $\mu$M ABA only slightly down-regulated CHRC expression. Neither ABA nor paclobutrazol markedly affected Psy mRNA levels.

To study the effect of protein synthesis inhibition on the up-regulation of CHRC by $GA_3$, the protein synthesis inhibitor cycloheximide (CHX) was used. For this purpose, cucumber flower buds were cultured with or without CHX in the presence of $GA_3$. Results are seen in FIG. 9.

Figure 9:
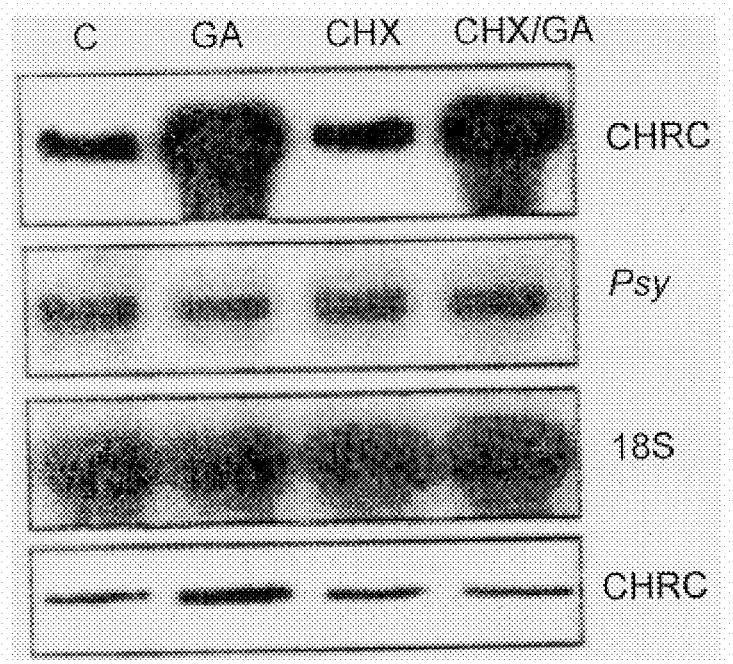
FIG. 9 shows effect of cyclohexamide on CHRC gene expression.

FIG. 9 shows effect of cycloheximide on CHRC gene expression. Total RNA and protein were extracted from cucumber corollas of flower buds cultured for 6 hours in the presence of 100 $\mu$M $GA_3$ (GA), 50 $\mu$M CHX following 2 hours of pretreatment with 50 $\mu$M CHX (CHX/GA), or no phytohormones (C). Northern (CHRC, Psy, and 18S) and Western (bottom panel) blot analyses were performed as described above.

As can be seen from FIG. 9, 50 $\mu$M CHX did not prevent the up-regulation of CHRC mRNA by $GA_3$, whereas it successfully abolished the increase in CHRC protein levels in $GA_3$-treated buds. CHX alone did not affect CHRC transcript accumulation, in contrast to its up-regulating effect on the early response GAmyb gene in barley aleurone cells. Psy mRNA levels in corollas were also unaffected by CHX treatment.

The sensitivity of CHRC expression to $GA_3$ was also assessed. For that purpose, a dose response curve ranging from $1\times10^{-8}$ to $1\times10^{-4}$ M $GA_3$ was obtained after exposing grown flower buds in vitro to the $GA_3$ for 2 hours. Results are seen in FIG. 10.

Figure 10:
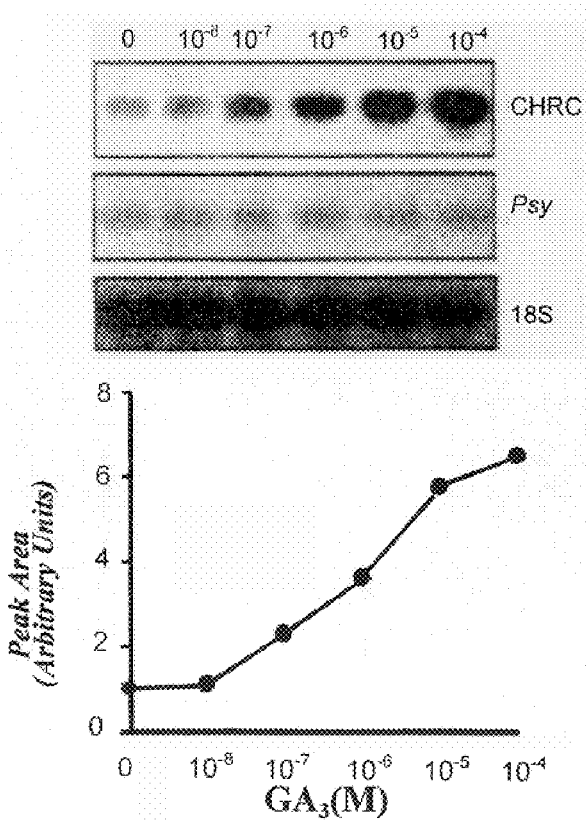
FIG. 10 shows a dose response of CHRC to $GA_3$.

In FIG. 10, flower buds were cultured for 2 hours without (0) or with various concentrations of $GA_3$. Total RNA was isolated from corollas, and a Northern blot was probed as above. The results of the CHRC Northern blot analyses are also shown graphically relative to the mRNA level of control corollas cultured without $GA_3$ (arbitrary value of 1).

As seen in FIG. 10, CHRC was strongly up-regulated at $10^{-5}$–$10^{-4}$ M, whereas concentrations as low as $10^{-7}$ M were sufficient to markedly elevate basal CHRC mRNA levels. A similar response curve has been described for the primary GA-responsive gene, pmyb92, in petunia.

In the studies described above, the upregulation of CHRC synthesis in response to $GA_3$ acid was observable already within 20 minutes. Such response was insensitive to protein synthesis inhibitor cycloheximide. Abscisic acid and paclobutrazol strongly down-regulated CHRC mRNA levels. CHRC mRNA accumulation in response to gibberellic acid displayed a dose-dependent increase up to $10^{-4}$ M gibberellic acid. The up-regulation could be detected with as little as $10^{-7}$ M gibberellic acid.

chrc gene is the first structural gene identified to date whose expression is regulated by $GA_3$ in a primary fashion. The rapid response of CHRC to $GA_3$ followed by increased carotenoid accumulation, and sequestration shows that such carotenoid accumulation is genetically regulated by the chrc gene which encodes CHRC proteins. A crucial role for GAs during flower development, chromoplastogenesis and carotenoid accumulation in C. sativus was discovered.

Control of carotenogenesis by $GA_3$ seems to be executed via regulation of downstream carotenoid biosynthesis enzymes and/or carotenoid sequestration. CHRC's rapid up-regulation in response to $GA_3$ is crucial for enhanced carotenoid accumulation in the chromoplast.

The method for production of carotenoids involves accumulation, sequestration or high production of the carotenoids in the plants chromoplasts or in bacterial or other cells by providing these cells with genetic apparatus for increased expression of CHRC protein which, as shown above is involved in greater accumulation, sequestration or carotenoid production. In practice, the plants or bacteria are transfected with chrc gene encoding CHRC protein and the expression of this protein is enhanced with $GA_3$ in combination with CHRC promoter in plants and with any suitable promoter in bacteria or other cells or tissue. In this way, the plants or bacteria accumulate large amounts of carotenoids which are harvested and purified as necessary for their intended use.

II. CHRD—A Minor Chromoplast-Specific Protein

In addition to CHRC protein, the invention also concerns discovery of chromoplast protein D (CHRD). Compared to CHRC protein, the CHRD protein of about 14 kD is minor in abundance. When the polypeptide compositions of chromoplasts, chloroplasts, and corollas at different developmental stages were determined and compared, the CHRD was present in chromoplasts, undetectable in chloroplasts, and accumulated in corollas in parallel with flower development as determined by Coomassie brilliant blue staining. Chromoplast protein D (CHRD) was isolated from cucumber corolla chromoplasts. Immunological characterization revealed that the protein is chromoplast-specific and that its steady-state level in corollas increases in parallel to flower development. The protein was not detected in cucumber leaves or fruits. Immunological analysis of corollas and fruits from a variety of other plants also did not reveal cross-reactivity with the CHRD protein antisera.

Similarly to the studies described for CHRC protein, $GA_3$ rapidly enhanced, whereas paclobutrazol down-regulated, the steady-state level of CHRD. Ethylene also down-regulated the protein's steady-state level. These results show that hormonal control of chromoplastogenesis is tightly regulated at the tissue/organ level. Results of the above studies are shown in FIGS. 11–15.

Figure 11:
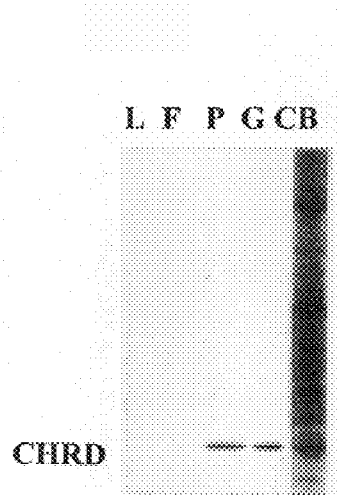
FIG. 11 shows immunodecoration of CHRD in different *Cucumis sativus* organs.

FIG. 11 shows immunodecoration of CHRD in different C. sativus organs. Total protein extracted from leaf (L), fruit (F), corolla (P) (50 $\mu$g per lane), and chromoplasts (C) (10 $\mu$g of protein) were electrophoresed on a 14% SDS-polyacrylamide gel and analyzed by Western blotting using antibodies against CHRD and alkaline phosphatase anti-rabbit 1 gG. CB, Coomassie brilliant blue-stained total proteins (25 $\mu$g) from chromoplasts.

Based on densitometry analyses, CHRD constitutes about 1% of the total chromoplast proteins resolved by SDS-PAGE. The protein was isolated and used to prepare antiserum, and the resultant antiserum cross-reacted with isolated CHRD and did not cross-react with isolated CHRC or chloroplasts. Preimmune serum did not reveal any signal when used in a western blot analysis of corollas, chromoplasts, or isolated CHRD. The affinity-purified antibodies against CHRD were found to be tissue-specific: they did not cross-react with the total protein fraction of cucumber leaves or fruits, whereas a strong signal was obtained with corollas and isolated chromoplasts.

Figure 13:
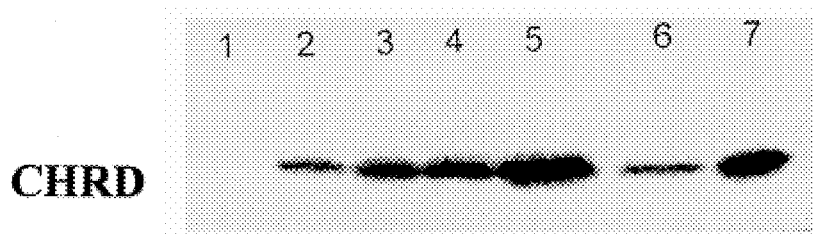
FIG. 13 shows changes in the immunologically detectable amounts of CHRD during flower development in vivo.

During flower development the immunologically detectable level of CHRD increased in corollas up to anthesis and then decreased to a low level, as seen in FIG. 13.

FIG. 13 shows changes in the immunologically detectable amounts of CHRD during flower development in vivo. Total protein (50 μg per lane) extracted from leaf (lane 1), corollas at stages 1 through 5 (lanes 2–6, respectively), and chromoplasts (10 μg, lane 7) was electrophoresed on a 14% SDS-polyacrylamide gel and analyzed by western blotting.

To examine the possible relationship between CHRD and chromoplast pigments, the plastids were solubilized with various detergent combinations and fractionated on a nondenaturing gel. Results are seen in FIG. 12.

Figure 12:
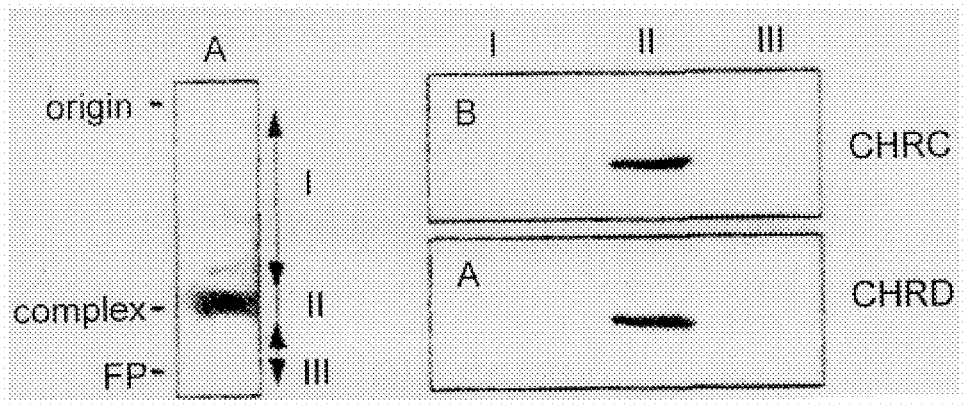
FIG. 12 shows identification of CHRD in the carotenoid-protein complex of chromoplasts.

FIG. 12 shows identification of CHRD in the carotenoid-protein complex of chromoplasts. Chromoplast membranes isolated from corollas at anthesis were solubilized with 2% n-octyl α-D-glucopyranoside, 1% n-nonyl α-D-glucopyranoside, 1% n-decyl α-D-glucopyranoside, and 0.3% SDS (w/v) and fractionated on a nondenaturing Deriphatpolyacrylamide gel for 30 minutes at 100 V. The gel was photographed without fixing or staining (A). The entire lane was excised from the gel and cut into three pieces (lanes I–III). Proteins were extracted from these gel slices, re-electrophoresed on a fully denaturing 14% SDS-polyacrylamide gel, and analyzed by western blotting using CHRC (B) and CHRD (C) antibodies, FP, Free pigment zone.

A distinct, slow-migrating, yellow band was revealed under the following solubilization conditions: 2, 1, 1, and 0.3%; 1, 1, 2, and 0.3%; or 1, 2, 1, and (w/v) octyl glucoside, nonyl glucoside, decyl glucoside, and SDS, respectively. Western blot analysis of the polypeptides extracted from this distinct band and resolved by fully denaturing SDS-PAGE revealed the presence of CHRD and CHRC (FIG. 12). Coomassie brilliant blue staining of the SDS gels revealed CHRC to be the major polypeptide associated with these yellow bands.

To test for CHRD antigenic counterparts in chromoplastogenic organs of other plants, CHRD antibodies were cross-reacted with fruits and petals of a variety of different plants. Unlike CHRC, which is abundant in several other flowers, CHRD antiserum did not cross-react with corollas of melon, watermelon, daffodil, or rose, or with fruits of pepper or tomato, or with carrot.

Effects of developmental and environmental factors on CHRD accumulation were further studied.

Previous studies have shown the usefulness of the in vitro bud culture system, which fully resembles flower development with respect to carotenoid and CHRC accumulation, for studies of the involvement of growth regulators in chromoplast biogenesis. This system was, therefore, used to study the developmental regulation of CHRD expression in corollas. Inclusion of $GA_3$ in the culture medium resulted in enhanced accumulation of CHRD, as seen in FIG. 14.

Figure 14A:
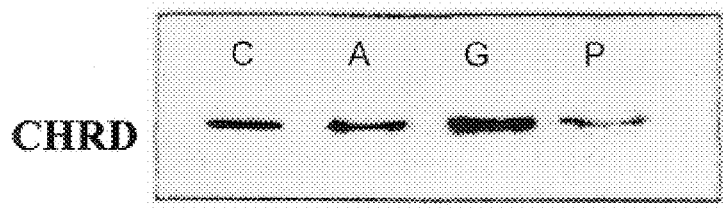
FIGS. 14A and 14B show effect of $GA_3$ on CHRD content of in vitro cultured corollas.
Figure 14B:
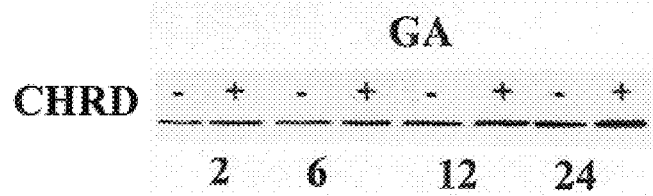

FIG. 14 shows effect of $GA_3$ on the CHRD content of in vitro cultured corollas. FIG. 14A shows young flower buds cultured for 72 hours in the presence of $GA_3$ (G), ABA (A), or paclobutrazol (P) or without phytohormones (C). CHRD levels in corollas were analyzed by western blotting (10 μg of total protein per lane) using antibodies against CHRD and horseradish peroxidase anti-rabbit IgG in an enhanced chemiluminescence detection system. FIG. 14B is a Western blot analysis of corollas (50 μg of total protein per lane) cultured for the indicated periods with (+) or without (−) $GA_3$. The blot was decorated with antibodies against CHRD and alkaline phosphatase anti-rabbit 1 gG.

When paclobutrazol, an inhibitor of $GA_3$ synthesis, was added to the in vitro bud culture system, the CHRD level per unit protein was down-regulated 4.8±0.2 times as compared with control untreated corollas. A lower level of CHRD was also detected in corollas treated with ABA, which is known to be antagonistic to $GA_3$ in several systems (2.5±0.3 times lower than that of control untreated corollas per unit protein), seen in FIG. 14A. The up-regulation of CHRD by $GA_3$ was very rapid, and after only 2 hours its level was markedly higher in treated versus untreated buds. No difference was noted in fresh weight or total protein level between treated and control corollas for up to 24 hours in culture.

The effect of ethylene, a growth regulator associated with fruit ripening and flower senescence on the accumulation of chromoplast-specific proteins is shown in FIG. 15.

Figure 15A:
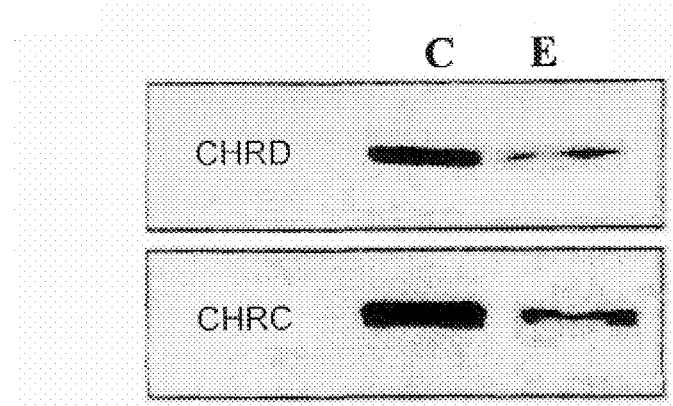
FIGS. 15A and 15B show effect of ethylene on CHRC and CHRD levels and effect of etiolation on CHRD levels in corollas.
Figure 15B:
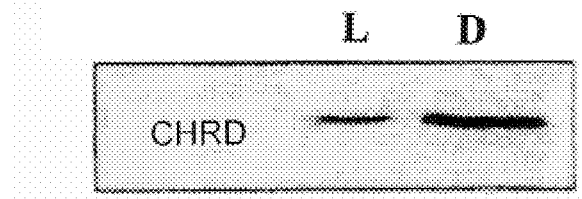

FIG. 15 shows the effect of ethylene or CHRC and CHRD levels and of etiolation on CHRD levels in corollas. In FIG. 15A, antibodies against CHRD or CHRC were used in a western blot analysis of CHRD and CHRC levels, respectively, in corollas cultured for 72 hours in the presence (E) or absence (C) of ethylene (50 μg of total protein per lane). In FIG. 15B, flowers were enclosed in aluminum foil in the greenhouse for 3 days and CHRD levels in etiolated (D) and control, nonetiolated (L) corollas were analyzed by western blotting (50 μg of total protein per lane).

As seen in FIG. 15A, the level of CHRD per unit protein was down-regulated following treatment with ethylene. Moreover, the level of CHRC in ethylene-treated corollas was also lower than that in controls.

Carotenoids, in contrast to chlorophyll, accumulate in the dark. To monitor the effect of light, CHRD levels in in vivo etiolated corollas were analyzed. FIG. 15B shows the CHRD level per unit protein in corollas of etiolated buds to be enhanced as compared with that in control corollas of light-grown buds. Effects of both ethylene and etiolation on CHRD levels normalized per corolla were even more pronounced, since the total protein content of the treated corollas was, respectively, 50% lower and 30% higher than that of control, untreated corollas.

Compared to CHRC, CHRD is only a minor protein, however, its function corresponds to CHRC function in carotenoids accumulation in chromoplasts.

III. The CHRC Promoter

The invention additionally concerns a discovery of a new CHRC promoter useful for directing of CHRC gene expression.

The new promoter was partly sequenced. The sequenced portion of the CHRC promoter has a sequence SEQ ID NO:10.

Figure 16:
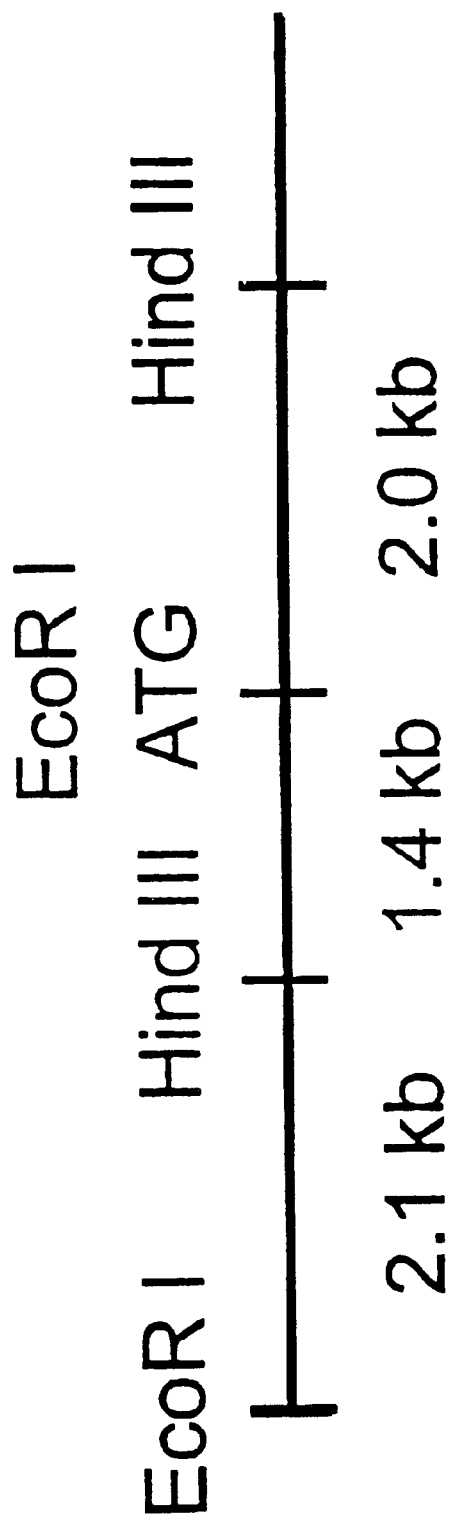
FIG. 16 shows a restriction map of the cloned genomic DNA containing the CHRC's coding and upstream regions

Briefly, a cucumber subgenomic library was prepared by digesting cucumber genomic DNA with Hind III and a clone containing the coding sequence for CHRC and its approximate 1.4 kb of the upstream region was isolated and sequenced. An approximately 2.1 kb DNA fragment 5' to the sequenced upstream region was also cloned. Cloning was performed using EcoRI-digested genomic DNA. Approximately 3.5 kb of the CHRC upstream region has been cloned as seen on the restriction map seen in FIG. 16. FIG. 16 shows a restriction map of the genomic DNA containing CHRC coding and upstream regions.

FIG. 16 is a reconstructed restriction map of genomic DNA fragment that contains upstream and coding regions of CHRC. 3'EcoRI site is approximately 150 nucleotides upstream to ATG. The sequence of the promoter region and the beginning of the transcribed region was obtained from cloned genomic HindIII fragment.

The sequenced upstream region was found to possess strong promoter activity and was found to be very efficient in the expression of a foreign gene GUS. The promoter containing CHRC upstream region was about 70% as efficient as the 35S CaMV promoter in cucumber petals and about 60% as efficient in leaves, fruits and stems. The CHRC promoter's efficiency in another representative of the cucurbit family, namely in melon, was similar to the efficiency found in cucumber.

Because CHRC gene expression is strongly regulated by a number of environmental and developmental signals, the cis elements within the promoter are very important and are, therefore, useful for generating and directing inducible and/or tissue specific gene expression in genes other than in Cucurbitacea.

Utility

The invention provides for high production and accumulation of carotenoids which are highly important to both animals and plants. Carotenoids produced according to the invention are used as essential dietary components added to the food for human consumption, as active ingredients of antioxidants and vitamins which possess anticancer activity and protect the human subjects from heart and age related diseases. Commercially, they are useful as food products colorants or as additives to pharmaceutical drugs. In agriculture, they are useful for enhancement of flower, fruit or plants colors. In photosynthetically active organisms, carotenoids are essential to the proper functioning of the light-harvesting apparatus and they determine color of fruits and flowers.

The current invention discloses a new gene for expression of proteins effecting accumulation and sequestration of carotenoids in plant chromoplasts. Derived from the new genes is a new promoter and a nucleotide sequence thereof which allows expression of any other foreign gene.

The invention is useful for production of plants producing large amounts of carotenoids. Carotenoids are important for medicinal purposes, as antioxidants, vitamin A precursors, food colorants, for production and variability of flower colors and as protective anti-cancer agents.

Production of carotenoids using expression of the discovered genes allows production of large quantities of carotenoids in a very practical and inexpensive way. Due to the presence of the carotenoid-binding domain within CHRC or CHRD, these proteins are potentially useful for efficient accumulation of carotenoids within any cell, not only those of plant origin.

The invention also enables production of carotenoids using the bacterial expression systems where CHRC or CHRD is introduced into bacteria in combination with enzymes for carotenoid biosynthesis, to increase the levels of accumulating carotenoids.

EXAMPLE 1

Plant Material

This example describes plant material used for the current studies. Cucumber (*Cucumis sativus* L.) plants (cultivar-Shimanon) obtained from Zeraim Gedera, Israel were grown under standard greenhouse conditions. Stages of flower development were as described in Plant Physiol. 104:321326 (1994): stages 1, 2, and 3 occurred 120, 72, and 24 hours before anthesis, respectively, stage 4 at anthesis, and stage 5, 24 hours after anthesis. All tissues were used immediately after collection or frozen in liquid nitrogen and stored at −70° C.

EXAMPLE 2

Plant Material and In Vitro Flower Bud Culture

This example describes plant material and conditions for in vitro flower bud culture. *C. sativus* L. plants (cultivar Shimahon, obtained from Zeraim Gadera, Israel) were grown under standard greenhouse conditions. In vitro culture of flower buds was performed at 23° C., under constant light from cool white fluorescent lamps with a photosynthetic photon flux density of 80 $\mu$mol/m$^2$ g, as described previously. Briefly, buds at developmental stage 1 (~8 mm in length, 120 hours before anthesis) were collected and rinsed several times with sterile water. Buds were then placed for 24 hours on a perforated Parafilm (American National Can, Greenwich, Conn.) covering a Petri dish filled with double-distilled sterile water, such that only the bases of the buds were in contact with the liquid. Following equilibration, buds were transferred to a fresh Petri dish (zero time for the experiments) and treated with GA$_3$, ABA, paclobutrazol, or CHX, as specified in the figure legends.

EXAMPLE 3

RNA Isolation and Northern Blot Analysis

This example describes conditions used for RNA isolation and Northern blot analysis. Total RNA from corollas of cucumber flower buds was isolated as described previously. RNA (15 and 25 $\mu$g) was fractionated through a 1.2% formaldehyde gel and transferred to a Hybond-N$^-$ filter (Amersham Corp.). A random priming kit (Boehringer Mannheim) was used to radioactively labeled DNA probes. The blots were hybridized with $^{32}$P-labeled cucumber CHRC cDNA (Vishnevetsky, et al., Plant Journal, 10: 1111–1118 (1996)) and reprobed with melon phytoene synthase (PSY) cDNA (MEL5), provided by D. Grierson of the Nottingham University, UK. The hybridization for analysis of CHRC expression was carried out in 0.263 M Na$_2$HPO$_4$, 7% SDS, 1 $\mu$M EDTA, 1% BSA for 16 hours at 60° C., and the washes were performed in 2×SSC/0.1% SDS at 50° C. followed by 2×SSC/0.1% SDS at 55° C., for 20 minutes each. Hybridization with the MEL5 probe was carried out at 55° C. using the same procedure. Following the hybridization, the blots were washed in 5×SSC/0.1% SDS at 45° C. for 20 minutes followed by 5×SSC/0.1% SDS at 50° C. and 2×SSC/0.1% SDS at 50° C. for 20 minutes each. Autoradiograms were quantified by scanning suitably exposed films in a densitometer (Molecular Dynamics, Sunnyvale, Calif.). The amount of RNA loaded onto the gels was standardized by optical measurement, by quantitation of the ethidium bromide fluorescence of cytoplasmic rRNA. and by the level of hybridization with a DNA fragment coding for cytoplasmic 18S RNA.

EXAMPLE 4

SDS-PAGE, Protein Digestion, Amino Acid Sequencing and Western Blotting

This example describes conditions used for SDS-PAGE, protein digestion, amino acid sequencing and Western blotting.

Chromoplast isolation and SDS-PAGE were performed as described in Plant Physiol. 102:491–496 (1993). The CHRC protein bands excised from SDS gels stained with Coomassie Blue were digested with *Staphylococcus aureus* V8 protease (Sigma), by placing gel slices containing the protein into the sample wells of a second SDS gel and then overlaying with the protease according to J. Biol. Chem. 252:1102–1106 (1977). Following electrophoresis, peptides were electrotransferred on to a polyvinylidene difluoride (PVDF) membrane obtained from Bio-Rad according to J. Biol. Chem. 262:10035–10038 (1987), stained with Coomassie Blue, and sequenced directly. Automated Edman sequencing was performed using an AB1 475A gas phase microsequencer (Applied Biosystems). The Western blot analyses were performed with an ECL Western blotting detection system (Amersham), using affinity-purified polyclonal antibodies against CHRC, Plant Physiol. 104:321–326 (1993) and horse-radish peroxidase anti-rabbit 1 gG (Sigma) as a second antibody.

EXAMPLE 5

PCR Amplification of cDNA Probe

This example describes PCR amplification procedure of cDNA probe.

Total RNA (40 µg) from corollas of stage 3 cucumber flower buds was isolated according to EMBO J. 7:1257–1263 (1988) and used for first-strand cDNA synthesis described in Molecular Cloning: A Laboratory Manual, Cold Spring Harbor, N.Y., Cold Spring Harbor Laboratory Press (1993). PCR amplification was performed using degenerate primers synthesized according to the amino acid microsequences of CHRC. Two forward primers were synthesized: 5'GGAATTCGAIAAITA(C/T)GGIGAIGA (SEQ ID NO:4), termed N, encoding the amino acid sequence EKYGD (SEQ ID NO:5) and having an EcoRI restriction site at its 5'-terminus, and 5'-GA(G/A)AATTCCCA(G/A)AC(C/T)AT(T/C)GAT (SEQ ID NO:6), termed F, encoding the amino acid sequence EISQTID (SEQ ID NO:7). The reverse primer used was 5'CA(A/G)(C/T)TGTGG(T/A)GTTCC(T/G)ATTA (SEQ ID NO:8), termed R, reflecting the complementary strand of DNA encoding the amino acid sequence IGTPQL (SEQ ID NO:9).

The first primer was synthesized according to the N-terminal amino acid microsequence of undigested CHRC, and the latter two were synthesized according to internal CHRC microsequences (Table 1).

The following reaction mixture was used for PCR: 50 mM KCl, 10 mM Tris-Cl pH 8.3, 1.0 mM $MgCl_2$, 60 µM of each dNTP, 0.4 µM of each primer and 1.5 units of Taq polymerase (Advanced Biotechnologies). The samples were heated to 94° C. for 2 minutes, followed by annealing at 50° C. for 2 minutes and elongation at 72° C. for 2 minutes. The amplification was continued for 30 cycles at 94° C. for 30 seconds, 55° C. for 1 minute, and 72° C. for 1 minute. After the last amplification cycle, the samples were incubated at 72° C. for 10 minutes. Following electrophoresis on a 2.0% agarose gel and subsequent purification (Jetsorb, Genomed Inc.), a 443 bp PCR product was cloned into pBluescript KS (Stratagene).

EXAMPLE 6

Construction and Screening of cDNA Library

This example describes conditions for construction and screening of cDNA library.

Poly(A)$^+$ RNA was purified from stage 3 flower corolla total RNA using PolyATract mRNA isolation system 1 (Promega), and 5 µg were used to construct a cDNA library in a Uni-Zap™ XR vector using a ZAP-cDNA® synthesis kit and Gigapack II packaging extracts (Stratagene). Approximately $10^5$ phages were screened with the radioactively labeled 443 bp PCR fragment and DNA was isolated from 15 positive clones. Hybridization was carried out for 16 hours at 65° C. and the filters were washed twice with 2×SSC/0.1% SDS at 65° C. (1×SSC=0.15 M NaCl/0.015 M trisodium citrate pH 7.0).

EXAMPLE 7

CHRC DNA Sequencing and Analysis

This example describes CHRC gene DNA sequencing and analysis.

Nucleotide sequences were determined by Dye Terminator Sequencing, using a Taq Dye Deoxy Terminator Cycle Sequencing Kit (Applied Biosystems). To avoid the sequencing errors that can occur with long DNA fragments (greater than 500 bp), the cDNA clones were sequenced using restriction fragments, and external (Bluescript) and internal (cDNA) specific primers in two directions each. DNA and protein sequences were analyzed using the GCG Wisconsin Package. Transmembrane protein predictions were based on PHDhtm (Neural Network System) according to J. Mol. Biol. 232:584–599 (1993) and TMpred Biol. Chem. Hoppe Seyer, 374:166 (1993) programs.

EXAMPLE 8

In Vitro Transcription Translation and Import Assay

This example describes transcription, translation and import assay.

The CHRC cDNA clone was subcloned into pSP73, which was then used as a template in a coupled transcription/translation system (Promega) containing SP6 RNA polymerase and wheat-germ extract. The reaction was performed in the presence of [$^3$H]-Leu (Amersham), to yield a radiolabeled precursor protein. Isolation of intact chloroplasts from pea seedlings, import reactions and detection of imported proteins were all performed as recently described in Plant Mol. Biol. 29:53–61 (1995). Fractionation of stroma and thylakoids, and alkali and protease treatments of thylakoids were performed as described in Plant Physiol. 99:247–255 (1992). pGEM4 Cab7 and pSP65 SSU were used to prepare Cab7 and SSU radio-labeled precursors, respectively, Plant Physiol. 102:35–42 (1993) and Plant Mol. Biol. 29:53–61 (1995). These were used as controls in the chloroplast uptake experiments. Post-important detection of proteins was performed by SDS-PAGE and fluorography.

EXAMPLE 9

Northern Blot Analysis

This example describes conditions used for Northern blot analysis.

Total RNA (10 µg) was fractionated through a 1.2% formaldehyde get and transferred to a Hybond-N$^+$ filter (Amersham). Membranes were probed with DNA fragments radio-actively labeled using a random priming kit (Boehringer Mannheim). The hybridization for analysis of CHRC expression during corolla development, presented in FIG. 10, was carried out in 0.263 M $Na_2HPO_4$, 7% SDS, 1 mM EDTA, 1% bovine serum albumin (BSA) for 16 hours at 60° C. and the washes were performed in 2×SSC/0.1% SDS at 50° C. for 20 minutes followed by 2×SSC/0.1% SDS at 55° C. Hybridization for other total RNA blots was carried out at 55° C. using the same hybridization procedure. Following the hybridization, the blots were washed in 5×SSC/0.1% SDS at 45° C. for 20 minutes followed by 5×SSC/0.1% SDS at 50° C. and 2×SSC/0.1% SDS at 50° C. for 20 minutes each. The amount of RNA loaded on to the gels was standardized by optical measurement, by quantitation of the ethidium bromide fluorescence of cytoplasmic rRNA and by the level of hybridization with a cytoplasmic rRNA probe coding for cytoplasmic 18S RNA, Plant Physiol. 104:321–326 (1993).

EXAMPLE 10

Chromoplast Specific Protein

This example describes preparation and testing of chromoplast specific protein of 14 kD (CHRD).

CHRD protein was isolated from *Cucumis sativus* as a minor component, immunologically characterised and analyzed in terms of the regulation of its expression by developmental signals using methods and conditions described above for CHRC. CHRD was found in chromoplasts, was undetectable in chloroplasts and accumulated in corollas in parallel to flower development. During flower development, the immunologically detectable levels of CHRD increased in corollas up to anthesis and then dropped to a low level. As with CHRC, the level of CHRD was found to be very rapidly upregulated by $GA_3$; after only 2 hours of culture, its levels were markedly higher in $GA_3$ treated compared to untreated buds. No difference was noted in fresh weight or total protein level between treated and control corollas for up to 24 hours in culture. When treated with abscisic acid (ABA), known $GA_3$ antagonist, or paclobutrazol, an inhibitor of $GA_3$ synthesis, was added to the in vitro bud-culture, CHRD levels were downregulated. Levels of both proteins, CHRC and CHRD were very strongly downregulated following treatment with ethylene, a growth regulator which promotes chloroplast-chromoplast conversion in fruits. The involvement of CHRD in carotenoid production, accumulation or sequestration in plants is further confirmed by the findings that the CHRD levels in corollas of etiolated buds was enhanced in darkness as compared to that in control corollas of light-grown buds. Carotenoids are known to accumulate in dark.

EXAMPLE 11

The CHRC Promoter

This example describes a sequencing of a new CHRC promoter for expression of CHRC and other foreign genes.

A cucumber subgenomic library was prepared by digesting genomic DNA with Hind III. A clone containing the coding sequence for CHRC and its approximate 1.4 kb of the upstream region was isolated and sequenced. In addition, approximately 2.1 kb DNA fragment 5' to the sequenced upstream region was also cloned. Cloning was performed using EcoRI-digested genomic DNA. As a result, approximately 3.5 kb of the CHRC upstream region has been cloned as seen on the restriction map (FIG. 16). The cloned promoter or a portion thereof has a sequence identified as SEQ ID NO:10.

The sequenced upstream region possessed strong promoter activity. In cucumber-petals, the CHRC upstream region was about 70% as efficient as the 35S CaMV promoter. In leaves, fruits and stems, the CHRC promoter was about 60% as efficient as 35S CaMV. Promoter's efficiency in melon was similar to that observed in cucumber.

What is claimed is:

1. An isolated nucleic acid comprising consecutive nucleotides which encode a protein which comprises consecutive amino acids having the sequence set forth in SEQ ID NO: 2.

2. The isolated nucleic acid of claim 1, wherein the consecutive nucleotides have the sequence set forth in SEQ ID NO:1.

3. An expression vector which comprises the isolated nucleic acid of claim 1 and at least one nucleic acid which is a regulatory sequence operably linked thereto.

4. The expression vector of claim 3, wherein the vector is a plasmid.

5. An expression vector which comprises pSP73 plasmid further containing the isolated nucleic acid of claim 1 operably linked to a regulatory sequence.

6. The expression vector of claim 3, wherein the nucleic acid which is a regulatory sequence is a promoter of CHRC gene expression comprising consecutive nucleotides having the sequence set forth in SEQ ID NO:10.

7. An isolated nucleic acid comprising consecutive nucleotides having the sequence of a promoter of CHRC gene expression as set forth in SEQ ID NO:10.

8. An expression vector comprising the nucleic acid of claim 7 operably linked to a second nucleic acid.

9. A method for generating CHRC gene expression in a bacterial cell which comprises transforming the bacterial cell with the expression vector of claim 3 wherein said regulatory sequence is operable in bacteria.

10. A method for increasing accumulation and sequestration of carotenoids in a plant cell comprising transfecting the cell with the nucleic acid of claim 1 operably linked to a nucleic acid which is a regulatory sequence enabling expression of the nucleic acid in the cell, so as to thereby increase the accumulation and sequestration of carotenoids in the plant cell.

11. The method of claim 10, wherein the nucleic acid which is a regulatory sequence is a promoter of CHRC gene expression comprising nucleotides having the nucleic acid sequence set forth in SEQ ID NO:10.

12. A method for generating tissue specific CHRC gene expression in a plant which comprises transfecting a cell which is present in the plant with the expression vector of claim 6, so as to thereby generate tissue specific CHRC gene expression in the plant.

13. A method of inducing gene expression in a cell which comprises transfecting the cell with the expression vector of claim 8, wherein said second nucleic acid is a gene, so as to thereby induce gene expression in the cell.

14. The method of claim 13, wherein the cell is a plant cell or a bacterial cell.

15. A method for generating tissue specific gene expression in a plant which comprises transfecting a cell which is present in the plant with the expression vector of claim 8, wherein said second nucleic acid is a gene, so as to thereby generate tissue specific gene expression in the plant.

\* \* \* \* \*